United States Patent
Nakayama et al.

(10) Patent No.: US 9,320,602 B2
(45) Date of Patent: Apr. 26, 2016

(54) COMPRESSED FIBER STRUCTURAL MATERIAL AND METHOD FOR PRODUCING THE SAME

(75) Inventors: Noboru Nakayama, Nagano (JP); Masaomi Horita, Nagano (JP); Naoki Izawa, Sapporo (JP); Hiroto Tamai, Inuyama (JP); Naoto Saito, Matsumoto (JP); Yuki Usui, Matsumoto (JP); Nobuhide Ogihara, Ina (JP)

(73) Assignee: SHINSHU UNIVERSITY, Matsumoto-shi, Nagano (JP)

( * ) Notice: Subject to any disclaimer, the term of this patent is extended or adjusted under 35 U.S.C. 154(b) by 258 days.

(21) Appl. No.: 14/345,668

(22) PCT Filed: Mar. 9, 2012

(86) PCT No.: PCT/JP2012/056063
§ 371 (c)(1),
(2), (4) Date: Jul. 8, 2014

(87) PCT Pub. No.: WO2013/042388
PCT Pub. Date: Mar. 28, 2013

(65) Prior Publication Data

US 2014/0336779 A1    Nov. 13, 2014

(30) Foreign Application Priority Data

Sep. 20, 2011 (JP) ................................ 2011-204955
Feb. 29, 2012 (JP) ................................ 2012-044751

(51) Int. Cl.
*A61F 2/28* (2006.01)
*C22C 49/11* (2006.01)
(Continued)

(52) U.S. Cl.
CPC . *A61F 2/28* (2013.01); *A61L 27/04* (2013.01); *B22F 3/002* (2013.01); *C22C 49/11* (2013.01);
(Continued)

(58) Field of Classification Search
CPC ... A61F 2/28; A61F 2/30; A61F 2310/00023; A61F 2310/00425; A61L 27/06; B22F 3/002; B22F 3/02; B22F 7/06; B22F 7/08; C22F 1/008; C22F 1/183; C22C 1/0458; C22C 14/00; C22C 49/11
See application file for complete search history.

(56) References Cited

U.S. PATENT DOCUMENTS 3,906,550 A * 9/1975 Rostoker ................ A61B 17/72
29/419.1

(Continued)

FOREIGN PATENT DOCUMENTS

JP      2002-069682 A  *  3/2002  .............. H01M 8/02
JP      2003-221603 A     8/2003
(Continued)

OTHER PUBLICATIONS

"4.3.3 Resorbable Bioactive High-Strength Bone Fixation Device," *Environment-Conscious Novel Material Series, Biomaterials*, The Ceramic Society of Japan, Nikkan Kogyo Shimbun, Ltd., 2008, pp. 236-237.

(Continued)

*Primary Examiner* — Edward Tolan
(74) *Attorney, Agent, or Firm* — Drinker Biddle & Reath LLP

(57) ABSTRACT

Provided is a method for easily producing a lamellar compressed fiber structural material which has mechanical characteristics close to those of in vivo bone and which is capable of easily increasing osteoblast even when a difference in strength exists. In order to solve the issues, the method for producing compressed fiber structural material 1, includes: a step of preparing biocompatible fiber 14 having an average diameter of 5 µm-50 µm and an aspect ratio of 20-500; and a step of molding compressed fiber structural material 1 by cold pressing/shearing biocompatible fiber 14, compressed fiber structural material 1 having an average pore diameter that is in the range of 60 µm-100 µm inclusive and a void fraction that is in the range of 25%-50% inclusive, both obtained by measurement in accordance with the mercury penetration method. Further, it is preferable for the cold pressing/shearing is performed by controlling a compressive pressure in the range of 200 MPa-2000 MPa, a shearing stroke length in the range of 0.2 mm-5 mm and a shearing velocity in the range of 0.5 mm/min-5 mm/min.

5 Claims, 14 Drawing Sheets

(51) Int. Cl.
B22F 3/00 (2006.01)
C22F 1/18 (2006.01)
A61L 27/04 (2006.01)

(52) U.S. Cl.
CPC ......... *C22F 1/183* (2013.01); *A61F 2002/2835* (2013.01); *A61F 2310/00023* (2013.01); *A61F 2310/00425* (2013.01)

(56) References Cited

U.S. PATENT DOCUMENTS

| | | | | |
|---|---|---|---|---|
| 5,030,233 | A * | 7/1991 | Ducheyne | A61F 2/30907 623/23.54 |
| 5,236,032 | A * | 8/1993 | Nukami | C22C 49/06 164/100 |
| 5,665,119 | A * | 9/1997 | Koller | A61F 2/28 140/107 |
| 7,794,851 | B2 * | 9/2010 | Vichniakov | C22C 47/068 427/180 |
| 7,927,708 | B2 * | 4/2011 | Mizrahi | B23K 11/11 428/213 |
| 8,383,187 | B2 * | 2/2013 | Rivard | A61F 2/30767 427/2.26 |
| 2006/0073181 | A1 | 4/2006 | Kuboki | |
| 2012/0233836 | A1 * | 9/2012 | Liu | A61L 27/06 29/419.1 |
| 2013/0211541 | A1 * | 8/2013 | Kerr | A61F 2/28 623/23.58 |

FOREIGN PATENT DOCUMENTS

| | | | | |
|---|---|---|---|---|
| JP | 2004-067547 | A | 3/2004 | |
| JP | 2012-172179 | A * | 9/2012 | ............... B22F 3/11 |
| WO | 2010-097413 | A1 * | 9/2010 | .... A61F 2310/00023 |

OTHER PUBLICATIONS

"B. Types, Structures, and Materials of Artificial Joints," *JSME Mechanical Engineers' Handbook (γ 9 Medical, Welfare, and Bio Systems).*, The Japan Society of Mechanical Engineers, 2008, pp. 131-132.

Fuse H., et al., "Consolidation of Magnesium Powder by Compression Shearing Method under Room Temperature," The Proceedings of the 37th Students Workshop of Hokuriku-Shinetsu Branch, The Japan Society of Mechanical Engineers (JSME), 2008, vol. 37th, pp. 75-76, 308, including English language translation of the abstract.

Hosonuma M., et al., "Process on the Porous Titanium Coating," Sixth World Conference on Titanium, 1998, vol. Proceedings—part 1, pp. 495-498.

Hayato Itahashi, et al., "Early Cellular Responses of Osteoblast-like Cells in vitro on Titanium Surfaces with Different Micromorphologies," The Japanese Society for Dental Materials and Devices (JSDMD), vol. 14, 1995, pp. 136-141.

Li, D. et al., "Geometry of artificial ECM, Three-Dimensional Structure of Titanium-Web (TW) Prmotes Differentiation of Human Bone Marrow Mesenchymal Cells into Osteoblasts," Journal of Hard Tissue Biology, 2005, vol. 14, No. 2, pp. 333-334.

Miyamoto R. et al., "Development of Artificial Bone (Ti/HAp) by Compression Shearing and Rotation Solidifying Method," The Proceedings of the 58th Japanese Joint Conference for the Technology of Plasticity, 2007, vol. 58th, pp. 215-216, including English language translation of the abstract.

Nakazawa M. et al., "Development of Ti/VGCF Composite of Compression shearing Method under Room Temperature," The Proceedings of the 61st Japanese Joint Conference for the Technology of Plasticity, 2010, vol. 61st, pp. 219-220, including English language translation of abstract.

Nakazawa M. et al., "Molding of Fibrous Titanium Thin Plate by Compression Shearing Method," The Proceedings of the 59th Japanese Joint Conference for the Technology of Plasticity, 2008, vol. 59th, pp. 433-434, including English language translation of abstract.

Ohashi S., et al., "Development of Layered method by Compression Shearing under Room Temperature," Proceedings of 39th Symposium on Stress-strain Measurement Strength Evaluation, The Japanese Society for Non-Destructive Inspection, Jan. 2008, pp. 109-114.

Bungo Otsuki, et al., "Pore throat size and connectivity determine bone and tissue ingrowth into porous implants: Three-dimensional micro-CT based structural analyses of porous bioactive titanium implants," Biomaterials 27, May 13, 2006, pp. 5892-5900.

Sugata A., et al., "Solidification of TI/HAP by Compression Shearing Method and Rotation Solidifying Method," The Proceedings of the Conference of the Japanese Society for Non-Destructive Inspeciation, 2008, vol. 2008, pp. 181-184, including English language translation of the abstract.

Norihiko Takada, Reconstruction of Maxillofacial Injuries with Dental Implants, Japanese journal of occupational medicine and traumatology, vol. 51, 2003, Apr. 10, 2003, pp. 324-329.

Hiroyuki Takeishi, et al., "Consolidation with Grain Refinement by Compression Shearing Method under Room Temperature," Journal of The Society of Materials Science, Japan, vol. 54, No. 3, Mar. 2005, pp. 233-238.

* cited by examiner (A)

(B)

(A)

(B)

(a) AR=25

(b) AR=100

(c) AR=250

(d) AR=500

(a) AR=25

(b) AR=100

(c) AR=250

(d) AR=500

(a) AR=25

(b) AR=100

(c) AR=250

(d) AR=500

(A)

(B)

(C)

COMPRESSED FIBER STRUCTURAL MATERIAL AND METHOD FOR PRODUCING THE SAME

FIELD OF THE INVENTION

The present invention relates to a compressed fiber structural material used as a biomaterial and a method for producing the same. In particular, the present invention relates to a lamellar compressed fiber structural material that has mechanical characteristics close to those of in vivo bone and that is used as a biomaterial capable of easily increasing osteoblast, and a method for producing the same.

BACKGROUND ART

Strength comparable to that of in vivo bone and an excellent binding with in vivo bone are required of biomaterials for artificial joints and dental implants, etc. Additionally, flexibility and bendability are required of biomaterials for reconstructing skull defects and biomaterials for orthopedically treating bone-grafted sites since they need to be adapted to the shape of the skull and the bone shape in such bone-grafted sites (Non-Patent Document 1).

Osteoblast is involved in the binding between biomaterials and in vivo bone. Osteoblast is known for its high surface roughness and its high initial attachment rate at its surfaces having three-dimensional and isotropic irregularities (Non-Patent Document 2). Moreover, osteoblast is known for the occurrence of an excellent ingrowth in materials having a sequence of pores with a diameter of a few tens of micrometers or more (Non-Patent Document 3). Accordingly, the more osteoblast is being easily attached and being easily grown, the more the binding between the biomaterials and in vivo bone excels.

Ceramics such as hydroxyapatite and the like are known as examples of biomaterials used for reconstruction of bone defects. Such ceramics are porous bodies produced through a powder metallurgical process and thus, they have an advantage of excellent binding with in vivo bone. However, they are not applied to highly loaded sites since they are less flexible and have low bending strength. Alumina (aluminum oxide), which is also a ceramic but with a higher strength, is required to be made porous in order to improve the binding with in vivo bone and reduce the bending elastic modulus. The porous alumina has disadvantages to the effect that it is less flexible and that the strength thereof is insufficient.

On the other hand, titanium materials have drawn attention as biomaterials for artificial joints and dental implants due to their excellent biocompatibility, strength and corrosion resistance. However, when a titanium plate is used as the titanium materials, there is an issue to the effect that such titanium plate has poor binding with in vivo bone due to its smooth surface. In order to address this issue, punched metal, which results from punching the titanium plate, has been used. Since titanium materials have a high specific strength, they have an advantage to the effect that the strength thereof is sufficient, even when they are punched to make them porous so as to improve binding with in vivo bone and to lower elastic modulus.

Further, medical materials have been proposed which make use of titanium fibers as the titanium materials and which also make use of non-woven fabric made from such titanium fibers (Patent Document 1). Such titanium non-woven fabric is made by intertwining and stratifying the titanium fibers having a diameter of less than 100 μm and an aspect ratio of 20 or more (i.e. the ratio of the short axis to the long axis=1:20 or more) and by forming space for implanting biological hard tissue from its surface into the interior thereof. Such titanium non-woven fabric has been proposed as a biological hard tissue-inducing scaffold material which is excellent in terms of biological hard tissue inductivity and fixity. Moreover, it has been proposed that such titanium non-woven fabric can be used together with orthopedic implants such as artificial dental root implants and artificial joint implants, etc.

Incidentally, examples of a method for solidifying and molding metal powder and fibers into porous bodies include a hot pressing process and a powder metallurgical process such as a spark plasma sintering process. However, the solidification and molding through such processes are associated with calefaction and heat generation. Such calefaction and heat generation cause oxidization and embrittlement of the compacts, and also the flexibility thereof becomes poor. On the other hand, a cold pressing/shearing process is a method in which metal powder and metal fibers are solidified and molded by being loaded with a compressive load and a shearing load in an air atmosphere at room temperature (Non-Patent Document 4 and Patent Document 2).

PRIOR ART REFERENCES

Non-Patent Documents

Non-Patent Document 1: Norihiko Takada, "Reconstruction of maxillofacial injures with dental implants," Japanese Journal of Occupational Medicine and Traumatology, 51, pp. 324-329 (2003)

Non-Patent Document 2: Hayato Itahashi, et al., "Early Cellular Responses of Osteoblast-like Cells in vitro on Titanium Surfaces with Different Micromorphologies," The Journal of the Japan Research Society of Dental Materials & Appliances, 14-1, pp. 136-141 (1995)

Non-Patent Document 3: Bungo Otsuki, et al., "Pore throat size and connectivity determine bone and tissue in growth into porous implants; Three-dimensional micro-CT-based structural analyses of porous bioactive titanium implants," Biomaterials, 27, pp. 5892-5900 (2006).

Non-Patent Document 4: Hiroyuku Takeishi, Noboru Nakayama, Hiroyuki Miki, "Consolidation with Grain Refinement by Compression Shearing Method under Room Temperature," Materials Science Research International, 54-3, pp. 233-238 (2005).

Non-Patent Document 5: "JSME Mechanical Engineer's Handbook—Applied System Edition (γ9, Medical, Welfare and Bio Systems)," The Japan Society of Mechanical Engineers, pp. 132 (2008).

Non-Patent Document 6: "Environment-Conscious-type new material series—Biomaterial" edited by the Ceramic Society of Japan, Nikkan Kogyo Shimbun, Ltd., pp. 237 (2008).

Patent Documents

Patent Document 1: Japanese Laid-Open Patent Application No. 2004-067547

Patent Document 2: Japanese Laid-Open Patent Application No. 2003-221603

SUMMARY OF THE INVENTION

Problems to be Solved by the Invention

When biomaterials made of titanium materials are used as biomaterials for reconstructing, for example, skull defects, and as biomaterials for orthopedically treating of bone grafted-sites, although such biomaterials already have high biocompatibility, high corrosion resistance and high binding with in vivo bone, which are possessed by the titanium materials themselves, they are also required to have mechanical characteristics (such as elastic modulus and strength) close to those of compact bone. In particular, it is necessary to prepare biomaterials that have desired mechanical characteristics according to the corresponding sites and people, such as when a difference in strength exists, depending on the sites to be treated, or also when a difference in bone strength from that of adult males exists for children, females and the elderly.

However, with the above-described conventional biomaterials, it is difficult to respond to such demands. For example, the punched metal, which results from punching the titanium plate, can be easily deformed due to its porosity; however, it still possesses strength as a plate material and thus, it cannot be used as either a biomaterial having mechanical characteristics close to those of compact bone or in cases where there is a difference in bone strength. In addition, the surface of the portions other than the punched holes is flat and fails to have a three-dimensional spatial structure, and thus, there exists an issue to the effect that an increase in osteoblast is insufficient.

In addition, the titanium non-woven fabric proposed in Patent Document 1 is made by sintering in a high-temperature vacuum and thus, the binding between the titanium fibers becomes strong due to such high-temperature sintering. The resulting titanium non-woven fabric, as a whole, has stiffness, and the flexibility thereof becomes poor. For this reason, it was difficult to let it to possess mechanical characteristics close to those of compact bone and thus, there also existed an issue to the effect that the cases in which a difference in bone strength exists cannot be addressed.

The present invention has been made in order to solve the above issues and the object thereof is to provide a method by which a lamellar compressed fiber structural material which has mechanical characteristics close to those of in vivo bone and which is capable of easily increasing osteoblast even when a difference in strength exists, depending on the sites to be treated, can be easily produced. Another object of the present invention is to provide a lamellar compressed fiber structural material used as a biomaterial which has mechanical characteristics close to those of in vivo bone and which is capable of easily increasing osteoblast.

Means for Solving the Problems

The inventors of the present invention have found, in the course of conducting research for solving the above issues, that when an attempt was made to mold a lamellar compressed fiber structural material by cold pressing/shearing the titanium fibers, it was found that the resulting compressed fiber structural material possessed biocompatibility and corrosion resistance, which are possessed by titanium itself, and further voids for easy generation of osteoblast, and further found that the cold pressing/shearing can easily adjust the strength of the compressed fiber structural material. When further consideration was made, similar knowledge was obtained for biocompatible fibers other than the titanium fibers, and the present invention was completed based on such knowledge.

The method for producing a compressed fiber structural material according to the present invention, for solving the above issues, includes: a step of preparing a biocompatible fiber having an average diameter of 5-50 μm and an aspect ratio of 20-500 and a step of molding a compressed fiber structural material by cold pressing/shearing the biocompatible fiber such that an average pore diameter is in the range of 60-100 μm inclusive and a void fraction is in the range of 25-50% inclusive, both obtained by means of measurement in accordance with the mercury penetration method.

According to the present invention, since the biocompatible fiber having an average diameter and an aspect ratio in the above-described ranges is used to mold into a compressed fiber structural material having an average pore diameter and void fraction in the above-described ranges through cold pressing/shearing, the produced compressed fiber structural material not only has high biocompatibility, which is possessed by the fiber itself, but it also possesses voids which can help osteoblast to form therein, and it can be utilized as a biomaterial having desired characteristics matched to those of the bone strength. As a result, even when a difference in strength exists, depending on the sites to be treated, a compressed fiber structural material having mechanical characteristics close to those of in vivo bone can still be produced. In addition, since the obtained compressed fiber structural material is provided with voids exhibiting the average pore diameter and void fraction in the above-described ranges, such voids allow the rate of osteoblast generation to be increased by double or more as compared to the conventional rate, and thus, the reconstruction of skull defects and the orthopedic treatment of bone-grafted sites are accelerated and a quick recovery time can be sought.

In addition, the cold pressing/shearing applied in the present invention can vary the mechanical characteristics, such as the elasticity and flexibility, of the obtained compressed fiber structural material by arbitrarily setting the compressive pressure, the shearing stroke length and the shearing velocity, etc., and thus, even when a difference in strength exists, depending on the sites to be treated, or when a difference in bone strength from that of adult males exists for children, females or the elderly, it is still possible to easily produce a compressed fiber structural material having mechanical characteristics useable for the respective sites and people, and thus, the cold pressing/shearing applied in the present invention is an extremely effective means. Examples of such characteristics include, for example, strength close to that of the patient's bone and any strength that allows the prevention of a weak site from being broken in the case where a strong site and a weak site are combined together and where the weak site is prone to breakage since the stress is concentrated thereon.

In the method for producing a compressed fiber structural material according to the present invention, it is preferable for the cold pressing/shearing to be performed by controlling a compressive pressure in the range of 200-2000 MPa, a shearing stroke length in the range of 0.2-5 mm and a shearing velocity in the range of 0.5-5 mm/min.

According to the present invention, since the cold pressing/shearing is performed by controlling the compressive pressure, the shearing stroke length and the shearing velocity, a compressed fiber structural material can be easily produced for child-oriented applications, elderly or female-oriented applications or adult-male-oriented applications, etc., depending on the processing conditions thereof.

In the method for producing a compressed fiber structural material according to the present invention, it is preferable for the cold pressing/shearing to be performed such that a bulk density is controlled so as to be in the range of 3-5 g/cm$^3$.

According to the present invention, by controlling the bulk density so as to be in the above-described range, the produced compressed fiber structural material can be applied to child-oriented applications, elderly or female-oriented applications or adult-male-oriented applications, etc.

In the method for producing a compressed fiber structural material according to the present invention, a titanium fiber is used as the biocompatible fiber, and a fiber selected from a magnesium fiber, a stainless steel fiber and a cobalt-chrome alloy fiber, or a powder selected from a titanium powder, a magnesium powder, a stainless steel powder and a cobalt-chrome alloy powder, is compounded therewith.

According to the present invention, in accordance with the applications of the compressed fiber structural fiber, a titanium fiber which excels in anticorrosion can be compounded with other fibers or powders. For example, the biocompatible fiber may be configured by compounding a titanium fiber with a magnesium fiber which can be removed by dissolving. As can be seen from the above, a compressed fiber structural material being of wide application can be produced by means of the cold pressing/shearing.

The compressed fiber structural material according to the present invention, for solving the above issues, is a structural material obtained by compressing and solidifying, without sintering, a biocompatible fiber having an average diameter of 5-50 μm and an aspect ratio of 20-500. Such compressed fiber structural material has an average pore diameter in the range of 60-100 μm inclusive and a void fraction in the range of 25-50% inclusive, both obtained by means of measurement in accordance with the mercury penetration method.

According to the present invention, since the biocompatible fiber having an average diameter and aspect ratio in the above-described ranges is compressed and solidified without sintering, and also since the average pore diameter and void fraction of the compressed and solidified compressed fiber structural material are in the above-described ranges, the compressed fiber structural material not only has high biocompatibility, which is possessed by the fiber itself, but it also possesses voids which can help osteoblast to form therein. Since the compressed fiber structural material according to the present invention is provided with voids exhibiting the average pore diameter and void fraction in the above-described ranges, such voids allow the rate of osteoblast generation to be increased by double or more as compared to the conventional rate, and thus, the reconstruction of skull defects and the orthopedic treatment of bone-grafted sites are accelerated and a quick recovery time can be sought. Moreover, since the average pore diameter and void fraction are in the above-described range, such compressed fiber structural material will have desired characteristics matched to those of the bone strength. As a result, even when a difference in strength exists, depending on the sites to be treated, or when a difference in bone strength from that of adult males exists for children, females or the elderly, a compressed fiber structural material still has mechanical characteristics usable for the respective sites and people and thus, is an extremely effective means.

In the compressed fiber structural material according to the present invention, it is preferable for a bulk density to be in the range of 3-5 g/cm$^3$.

According to the present invention, the compressed fiber structural material having a bulk density in the above-described range can be applied to child-oriented applications, elderly or female-oriented applications or adult-male-oriented applications, etc., depending on the value thereof.

In the compressed fiber structural material according to the present invention, a titanium fiber is used as the biocompatible fiber, and a fiber selected from a magnesium fiber, a stainless steel fiber and a cobalt-chrome alloy fiber, or a powder selected from a titanium powder, a magnesium powder, a stainless steel powder and a cobalt-chrome alloy powder, is compounded therewith.

According to the present invention, in accordance with the applications of the compressed fiber structural fiber, a titanium fiber which excels in anticorrosion can be compounded with other fibers or powders. For example, the biocompatible fiber may be configured by compounding a titanium fiber with a magnesium fiber which can be removed by dissolving. As can be seen from the above, a compressed fiber structural material being of wide application can be provided by means of the cold pressing/shearing.

Effect of the Invention

According to the method for producing a compressed fiber structural material according to the present invention, since a compressed fiber structural material having an average pore diameter and void fraction, both obtained by means of measurement in accordance with the mercury penetration method, in the above-described ranges, the produced compressed fiber structural material not only has high biocompatibility, which is possessed by the fiber itself, but it also possesses voids which can help osteoblast to form therein, and it can be utilized as a biomaterial having desired characteristics matched to those of the bone strength. As a result, even when a difference in strength exists, depending on the sites to be treated, a compressed fiber structural material having mechanical characteristics close to those of in vivo bone can still be produced. In addition, since the obtained compressed fiber structural material is provided with voids exhibiting the average pore diameter and void fraction in the above-described ranges, such voids allow the rate of osteoblast generation to be increased by double or more as compared to the conventional rate, and thus, the reconstruction of skull defects and the orthopedic treatment of bone-grafted sites are accelerated and a quick recovery time can be sought.

In addition, the cold pressing/shearing applied in the present invention can vary the mechanical characteristics, such as the elasticity and flexibility, of the obtained compressed fiber structural material by arbitrarily setting the compressive pressure, the shearing stroke length and the shearing velocity, etc., and thus, even when a difference in strength exists, depending on the sites to be treated, or when a difference in bone strength from that of adult males exists for children, females or the elderly, it is still possible to easily produce a compressed fiber structural material having mechanical characteristics useable for the respective sites and people, and thus, the cold pressing/shearing applied in the present invention is an extremely effective means. Examples of such characteristics include, for example, strength close to that of the patient's bone and any strength that allows the prevention of a weak site from being broken in cases where a strong site and a weak site are combined together and where the weak site is prone to breakage since the stress is concentrated thereon.

BRIEF DESCRIPTIONS OF THE DRAWINGS

EMBODIMENTS OF THE INVENTION

Hereinafter, a compressed fiber structural material according to the present invention and a method for producing the same will be described with reference to the drawings; however, the present invention is not limited only to the content described in the descriptions below and the drawings.

Figure 1:
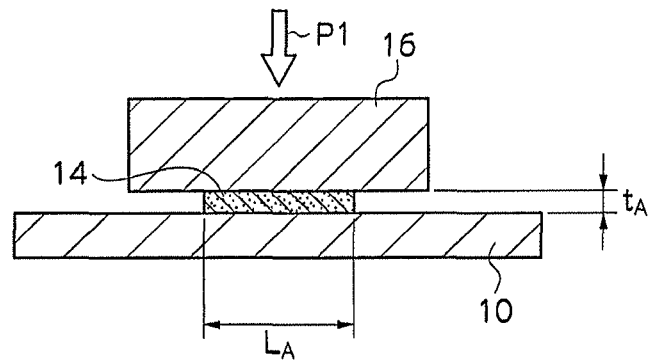
FIG. 1 is a diagram illustrating the principles of cold pressing/shearing which is applied in a method for producing a compressed fiber structural material according to the present invention.
Figure 1:
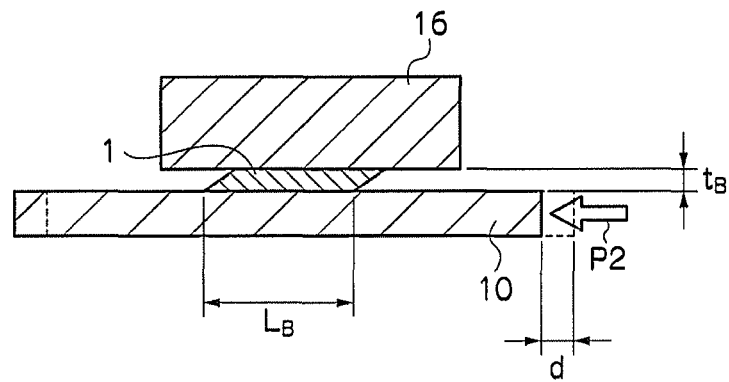
Figure 2:
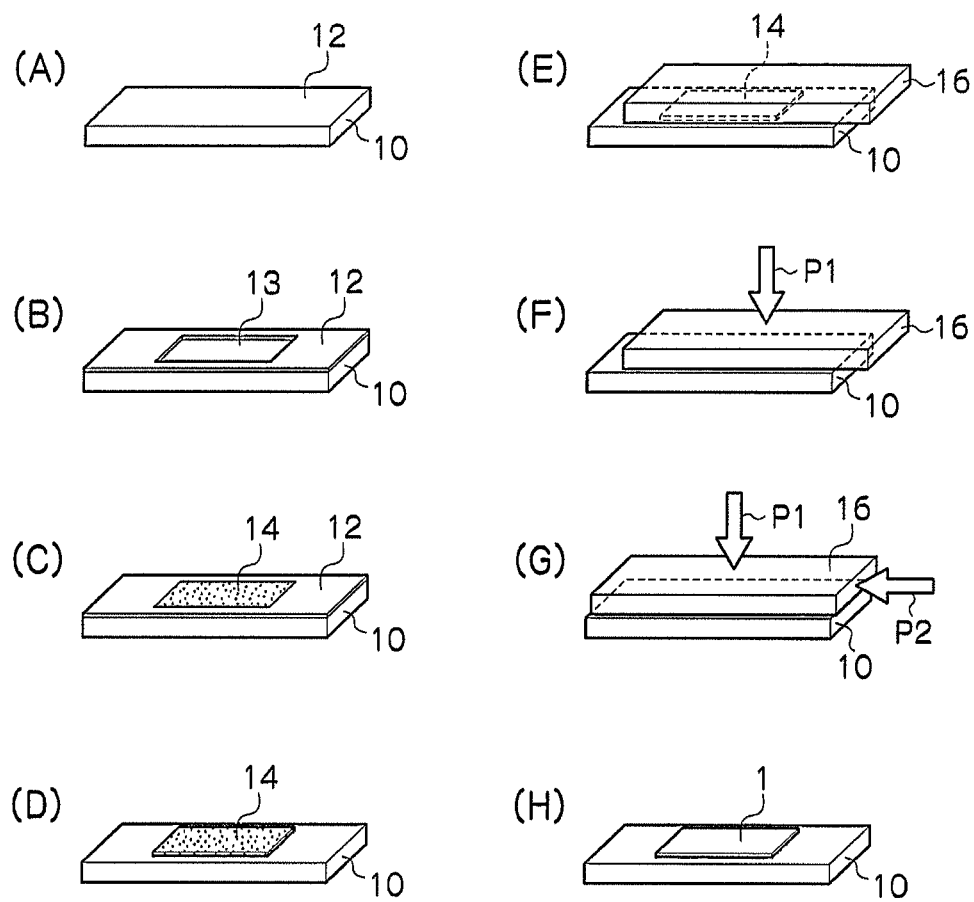
FIG. 2 is a process flow diagram illustrating an example of a method for producing a compressed fiber structural material according to the present invention.

As shown in FIGS. 1 and 2, the method for producing compressed fiber structural material 1 according to the present invention includes a step of preparing biocompatible fiber 14 and a step of molding compressed fiber structural material 1 by cold pressing/shearing biocompatible fiber 14. In this production method, a feature lies in the point of a fiber having an average diameter of 5-50 μm and an aspect ratio of 20-500 being used as biocompatible fiber 14 to mold, by cold pressing/shearing, compressed fiber structural material 1 such that an average pore diameter is in the range of 60-100 μm inclusive and a void fraction is in the range of 25-50% inclusive, both obtained by beams of measurement in accordance with the mercury penetration method. Hereinafter, a detailed description will be provided.

(Preparation Step)

In the preparation step, biocompatible fiber 14 having an average diameter of 5-50 μm and an aspect ratio of 20-500 is prepared. The term "biocompatibility" can be considered as referring to a behavior or tendency of having a good affinity with biological tissue and biological cells of humans and animals, etc. and by which a biological body would not recognize the material as being a foreign body. Accordingly, biocompatible fiber 14 in the present invention refers to a fiber having such behavior or tendency.

Biocompatible fiber 14 is not particularly limited as long as it is a fiber having biocompatibility, as represented by a titanium fiber, and it may include other fiber materials. Examples include any fiber selected from a magnesium fiber, a stainless steel fiber and a cobalt-chrome alloy fiber. These fibers may be used alone or may be used by compounding two or more kinds thereof. In particular, it is preferable for a titanium fiber to be used alone or to be used as the main fiber.

The titanium fiber excels in biocompatibility, has an extremely small amount of elution of metallic ions, is further light-weighted and is made of strong titanium or titanium alloy. Thus it is, in particular, preferably used. The composition of titanium is not particularly limited, and any titanium may be used regardless of whether it is pure titanium or any of various titanium alloys. For titanium alloys, for example, a Ti—Al based alloy (α-stabilizing type) may be preferably used; however, other titanium alloys may be used that are usable as biomaterials. Other titanium alloys include a Ti—Mn based alloy (β-eutectoid type), a Ti—Cr based alloy (β-eutectoid type) and a Ti—V based alloy (β-all solid solution type), etc. In particular, pure titanium based or Ti—Al based Ti-6Al-4V alloy is easily available and has an advantage to the effect that it has mechanical characteristics in which the strength thereof is adaptable to bone strength by cold pressing/shearing and thus, it is preferably used.

It should be noted that each of a magnesium fiber, a stainless steel fiber and a cobalt-chrome alloy fiber, etc. may be used alone; however, they may be preferably used by compounding together with a titanium fiber, as necessary. For example, a biocompatible composite fiber may be obtained having a magnesium fiber or a stainless steel fiber in the range of 0-100% by mass and a titanium fiber in the range of 100-0% by mass.

As for the dimensions of biocompatible fiber 14, it preferably has an average diameter in the range of 5-50 μm and an aspect ratio in the range of 20-500. In the present invention, compressed fiber structural material 1 is molded, by cold pressing/shearing, which has mechanical characteristics close to those of in vivo bone. In the present invention, in order to obtain such compressed fiber structural material 1, biocompatible fiber 14 having an average diameter in the range of 5-50 μm and an aspect ratio in the range of 20-500 is used to obtain compressed fiber structural material 1 having desired mechanical characteristics close to those of in vivo bone.

The term "average diameter" refers to a value obtained by averaging the diameters of the individual fibers. The expression "diameter of a fiber" refers to a diameter in a cross section of the fiber. When the cross section of the fiber is circular, it refers to a "diameter" of the individual fiber, when the cross section of the fiber is oval-shaped, it refers to a "diameter obtained by averaging the length along the major axis and the length along the minor axis," and when the cross section of the fiber is either rectangular or has an irregular shape, it refers to the diameter of a circle having the area of a circle which is converted from the area of such rectangular or irregular shape. The titanium fiber employed in the embodiments described below has a rectangular cross section, and thus, the average diameter used herein refers to a value obtained by calculating the cross sectional area from the cross sections of the individual fibers, determining a diameter of a circle having the same cross sectional area as the calculated cross sectional area, and by averaging the diameter values measured for a plurality of fibers.

When biocompatible fiber 14 has an average diameter of less than 5 μm, there is an issue to the effect that such fiber will not be easily accessible. On the other hand, when biocompatible fiber 14 has an average diameter of over 50 μm, the fiber will be too thick so that the strength of molded compressed fiber structural material 1 will be too large and thus, the strength value thereof may depart from the strength value of in vivo bone.

When biocompatible fiber 14 has an aspect ratio of over 500, the length with respect to the diameter will be too large so that the handling thereof will become difficult, and the strength of molded compressed fiber structural material 1 will become too large and thus, the strength value thereof may depart from the strength value of in vivo bone. On the other hand, when biocompatible fiber 14 has an aspect ratio of less than 10, there will be issues to the effect that the length with respect to the diameter will be too small so that the flexibility of molded compressed fiber structural material 1 will be reduced and thus, it will become brittle and be difficult to handle, as well as being difficult for the void fraction to fall within a predetermined range.

The dimensions of such biocompatible fiber 14 are specified in consideration of the mechanical characteristics of compressed fiber structural material 1 after being molded by cold pressing/shearing. However, the availability and the ease of handling of the fibers are also taken into consideration and thus, it is preferable that the dimensions are within the above-described ranges, regardless of the fiber materials.

Biocompatible fiber 14 may be prepared by purchasing various marketed fibers having predetermined dimensions or may be prepared by, after cutting a sheet (for example, a titanium sheet, etc.) having a predetermined thickness and making the cut sheet into a fibrous form, cutting the fibers so as to have a predetermined length.

In the present invention, biocompatible fibers may be compounded with each other, as described above, or a biocompatible fiber may be compounded with a biocompatible powder. Examples of biocompatible fibers to be compounded include a titanium fiber, a magnesium fiber, a stainless steel fiber and a cobalt-chrome alloy fiber, etc. Examples of biocompatible powders to be compounded include a titanium powder, a magnesium powder, a stainless steel powder and a cobalt-chrome powder, etc. The selection of the fibers and powders to be compounded depends on the application and usage, etc. of compressed fiber structural material 1 obtained through such compounding.

As an example, a titanium fiber may be compounded with a magnesium fiber or a magnesium powder. Magnesium is a biocompatible substance and is also a substance that dissolves over time through reaction with biological liquids. For this reason, it may be preferably used for cases in which a certain degree of strength is required at the time of use but it is better that the strength thereof reduces over time. In particular, ceramic porous bodies have an advantage to the effect that the strength thereof improves along with the regeneration of bone cells. However, such ceramic porous bodies have an issue to the effect that the initial strength at the time of implantation into the human body is low. Accordingly, it is preferable for there to be a composite material that has a predetermined strength at the time of implantation into the human body and for the strength to reduce over time after the implantation.

In response to such demand, it is possible to provide compressed fiber structural material 1 which is made by compounding, for example, a titanium fiber with a magnesium fiber or a magnesium powder, which dissolves over time in vivo and wherein, further, the dissolved elements thereof do not affect the biological body. Obtained compressed fiber structural material 1 has an advantage to the effect that it can be designed to have a predetermined strength at the time of implantation into the human body and to reduce the strength thereof over time through the dissolution of magnesium after the implantation. In addition, voids that allow for easy generation of osteoblast are formed as a result of the magnesium dissolution. In particular, according to the present invention, compressed fiber structural material 1 is produced through cold pressing/shearing, and thus, it can be designed to have a desired strength by controlling the fiber diameter, the particle diameter, the compounding quantity, the compounding ratio and the compressive pressure, etc. Moreover, since no heat, such as that applied in regular casting, etc., is applied, it is possible to prevent titanium and magnesium from becoming alloyed and thereby being unable to dissolve.

For example, a composite material may be made by blending a titanium fiber with a magnesium fiber or a magnesium powder and then by performing the cold pressing/shearing on the blend, or, as will be described in the Examples below, a composite material may be made by secondary-molding the primary compressed compact of the titanium fiber after depositing a magnesium powder thereon. It should be noted that, in the Examples below, a three-layered structure is presented with a primary compressed compact of a titanium fiber sandwiched between magnesium powders or primary compression compacts thereof; however, a double-layered structure is also possible wherein a primary compressed compact of a titanium fiber and a magnesium powder or a primary compression compact thereof are deposited on each other.

The fibers to be used, such as a titanium fiber and a magnesium fiber, etc., preferably have an average diameter and an aspect ratio within the above-described ranges. In addition, in terms of the powders to be used, such as a magnesium powder, etc., those that have a particle diameter in the range of approximately 20-200 μm and that have various shapes, such as a spherical form, a non-spherical form and a massive form, can be used. In addition, the cold pressing/shearing can be performed with the same means and conditions as those for the material made of only fibers in the molding process described below.

As described above, depending on the application of compressed fiber structural material 1, an anticorrosive titanium fiber is compounded with a magnesium fiber or a magnesium powder so as to allow compressed fiber structural material 1 to have the above described functions. Similarly, by compounding while utilizing the characteristics of the elements to be compounded, compressed fiber structural material 1 can be applied to new applications and usages.

(Molding Process)

As shown in FIGS. 1 and 2, the molding process is a process in which the above-described biocompatible fiber 14 goes through cold pressing/shearing to be molded into compressed fiber structural material 1. The "cold pressing/shearing" applied in the present invention is a molding method which has been reported by the inventors (see Non-Patent Document 4 and Patent Document 2) and in which compressed fiber structural material 1 is solidified and molded by loading biocompatible fiber 14 with compression load P1 and shearing load P2 in an air atmosphere at room temperature. In this method, it is considered that an oxide layer of biocompatible fiber 14 is broken by the loading of compression load P1 and shearing load P2 and that the solidification is achieved through the binding between the surfaces that are newly formed through the breakage of such oxide layer and thus, it is said that the solidification and molding at room temperature are possible without heating from the outside. However, in the present invention, a large load for breaking the oxide layer is not necessarily required and it is only necessary to add compression load P1 and shearing load P2 sufficient to allow the fibers/powders to intertwine with each other.

This cold pressing/shearing has an advantage to the effect that, since solidification and molding are performed at room temperature, it is possible to mold biocompatible fiber 14 while keeping its fibrous form and to produce porous compressed fiber structural material 1 having a sufficient strength. Moreover, since the surface of molded compressed fiber structural material 1 will be porous, having three-dimensional irregularities, there is also an advantage to the effect that molded compressed fiber structural material 1 becomes a biomaterial having high binding with in vivo bone. In addition, the interior of molded compressed fiber structural material 1 has predetermined voids, and thus, the blood-derived cells entered into the voids go through cell differentiation from mesenchymal cells to osteoblast under certain conditions and then mature into bone cells and bone tissue similar to the surrounding healthy bone tissue over time from young bone cells.

It should be noted that the term "room temperature" means no aggressive heating is provided and is a term which goes against high-temperature sintering where aggressive heating is provided. In the present invention, such term is used to encompass the range of approximately 20-100° C., and it typically refers to the range of approximately 20-80° C. The term "air atmosphere" means an uncontrolled atmosphere, and it refers to an air atmosphere without any pressurization or depressurization. However, as long as it is a similar atmosphere, such term may refer to any atmosphere in which pressurization or depressurization is performed to control to a gas environment comparable to that of air.

Such cold pressing/shearing allows for an easy adjustment of the strength of compressed fiber structural material 1. Such strength adjustment can be achieved, as illustrated in FIG. 1, by varying the processing conditions such as the compressive pressure P1, the shearing stroke length d and the shearing velocity, etc. The preferable conditions vary depending on the material and dimensions of biocompatible fiber 14, which is the raw material, and thus, they cannot be generally defined. However, from the perspective of making the strength of compressed fiber structural material 1 close to that of in vivo bone, it is typically preferable for compressive pressure P1 to be within the range of 200-2000 MPa, the shearing stroke length d to be within the range of 0.2-5 mm and the shearing velocity to be within the range of 0.5-5 mm/min. By setting the respective conditions within these ranges, compressed fiber structural material 1 having mechanical characteristics close to those of in vivo bone can be obtained.

A representative molding process of compressed fiber structural material 1 will be described below. FIG. 1 is a diagram illustrating the cold pressing/shearing and FIG. 2 is a flow diagram illustrating an example of a method for producing compressed fiber structural material 1 according to the present invention.

The cold pressing/shearing is a method in which, as shown in FIG. 1(A), compressive stress P1 is applied, through moving plate 16, to biocompatible fiber 14 which is sandwiched between fixed plate 10 and moving plate 16, and under the condition where such compressive stress P1 is applied, as shown in FIG. 1(B), fixed plate 10 is moved in a lateral direction and shearing stress P2 is applied to biocompatible fiber 14 so as to obtain compressed fiber structural material 1. Here, "$t_A$" denotes the fill height of biocompatible fiber 14, "$L_A$" denotes the fill length of biocompatible fiber 14, "$t_B$" denotes the thickness of obtained compressed fiber structural material 1 and "$L_B$" denotes the length of obtained compressed fiber structural material 1. In addition, "d" denotes the shearing stroke length over which fixed plate 10 moves in a lateral direction.

When producing compressed fiber structural material 1, as shown in FIG. 2, fixed plate 10 is first prepared (FIG. 2(A)) and then penetrated mold 12 provided with penetration hole 13 having predetermined dimensions is placed on fixed plate 10 (FIG. 2(B)). Subsequently, biocompatible fiber 14 is filled in penetration hole 13 (FIG. 2(C)), and then penetrated mold 12 is removed (FIG. 2(D)). Subsequently, fixed plate 10 having biocompatible fiber 14 placed thereon is installed in cold pressing/shearing device 20 (see FIG. 3) and moving plate 16 is placed on biocompatible fiber 14 (FIG. 2(E)). Subsequently, cold pressing/shearing device 20 (see FIG. 3) is activated to load biocompatible fiber 14 with compressive stress P1 (also referred to as a compression load) (FIG. 2(F)). Compressive stress P1 at this point is measured with a load cell (See FIG. 3) installed at the upper portion of the device. Subsequently, while remaining loaded with compressive stress P1, moving plate 16 is moved in a lateral direction to load biocompatible fiber 14 with shearing stress P2 (also referred to as a shearing load) (FIG. 2(G)). Lastly, compressive stress P1 and shearing stress P2 are released and moving plate 16 is removed, and then compressed fiber structural material 1 is obtained (FIG. 2(H)).

Figure 3:
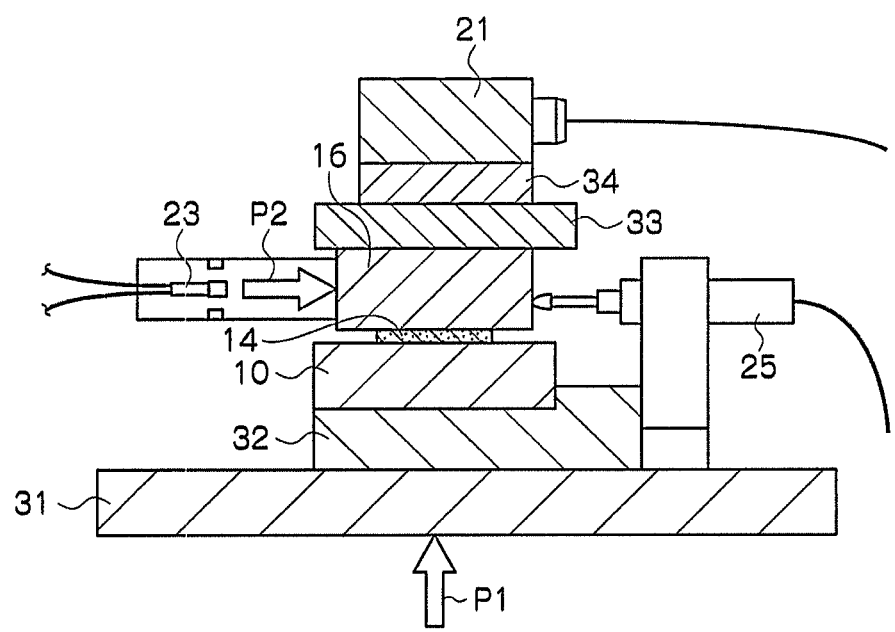
FIG. 3 is a configuration diagram illustrating an example of a cold pressing/shearing device used in a method for producing a compressed fiber structural material according to the present invention.

It should be noted that, in FIG. 2, the configuration is such that compressive stress P1 is applied from the above and shearing stress P2 is applied from the right side; however, as shown in cold pressing/shearing device 20 in FIG. 3, the configuration may also be such that compressive stress P1 is applied from the bottom and shearing stress P2 is applied from the left side.

(Device)

The device for cold pressing/shearing compressed fiber structural material 1 is not particularly limited; however, FIG. 3 provides an example of cold pressing/shearing device 20 consisting of a basic structure. In cold pressing/shearing device 20 shown in FIG. 3, fixed plate 10 and moving plate 16 are arranged and biocompatible fiber 14 is sandwiched therebetween. Fixed plate 10 and moving plate 16 are held by plates 31-34 from the top and the bottom. Compressive stress P1 may be measured, for example, with load cell 21 arranged at the top and shearing stress P2 may be measured, for example, by a four-active gauge method (a perpendicular alignment method) using four strain gauges 23 arranged on moving plate 16. In addition, the shearing stroke length may be measured using displacement gauge 25 and the shearing velocity may be calculated from such result.

Figure 4:
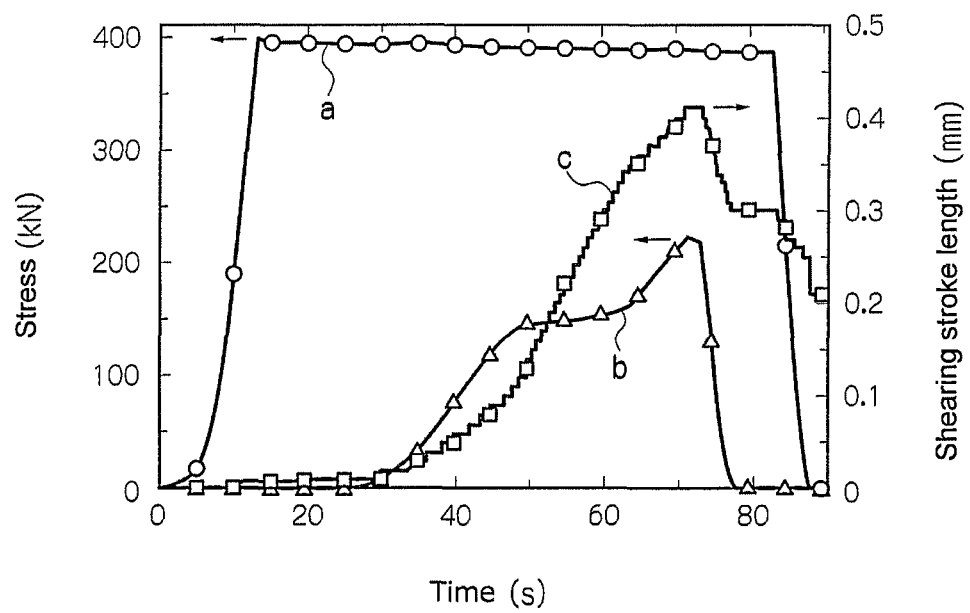
FIG. 4 shows an example in which a compressive stress, a shearing force and a shearing stroke length are represented.

FIG. 4 is a graph illustrating compressive stress P1, shearing stress P2 and the shearing stroke length at the time of cold pressing/shearing. In FIG. 4, "a" denotes compressive stress P1, "b" denotes shearing stress P2 and "c" denotes the shearing stroke length. As shown in FIG. 4, when, under the condition in which compressive stress P1 of, for example, 400 kN is applied to biocompatible fiber 14, fixed plate 10 starts to move in a shearing direction, shearing stress P2 occurs simultaneously and shearing processing is performed.

Figure 5:
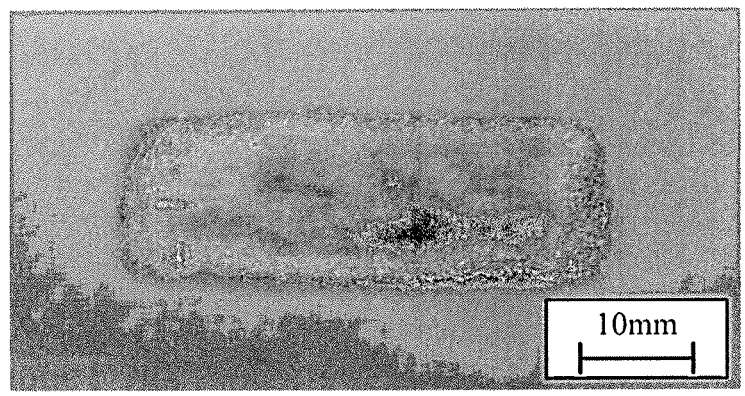
FIG. 5 is a photograph seen from a top-down view of an example of a compressed fiber structural material according to the present invention.

FIG. 5 shows an example of compressed fiber structural material 1 obtained by the cold pressing/shearing. The size and thickness of compressed fiber structural material 1 are not particularly limited and they can be adjusted according to the size of penetrated mold 12 (see FIG. 2) to be filled with biocompatible fiber 14 and the fill amount of biocompatible fiber 14 therein. It should be noted that, in FIG. 4, under the condition in which compressive stress P1 of 400 kN (i.e. 1000 MPa) is applied, the shearing stress was loaded until the shearing distance reached 0.4 mm. At this point, shearing stress P2 reached up to approximately 250 kN and thereafter, the shearing distance shrank to 0.2 mm.

(Compressed Fiber Structural Material)

Compressed fiber structural material 1 molded by the above-described method is a structural material in which biocompatible fiber 14 having an average diameter of 5-50 µm and an aspect ratio of 20-500 is compressed and solidified without sintering. The feature of such compressed fiber structural material 1 lies in the point to the effect that an average pore diameter thereof is in the range of 60-100 μm inclusive and a void fraction thereof is in the range of 25-50% inclusive, both obtained by performing measurement in accordance with the mercury penetration method on compressed fiber structural material 1.

Since biocompatible fiber 14 having an average diameter and an aspect ratio in the above-described ranges is compressed and solidified without sintering and since the volume of the pores in compressed and solidified compressed fiber structural material 1 is in the above-described range, compressed fiber structural material 1 has desired mechanical characteristics matched to the bone strength. As a result, even when a difference in strength exists, depending on the sites to be treated, or when a difference in bone strength from that of adult males exists for children, females or the elderly, it is still possible to mold compressed fiber structural material 1 having mechanical characteristics useable for the respective sites and people and thus, it is extremely effective. In addition, compressed fiber structural material 1 has high biocompatibility, which is possessed by biocompatible fiber 14 itself, and is provided with voids exhibiting the average pore diameter and void fraction in the above-described ranges, and thus, such voids allow the rate of osteoblast generation to be increased by double or more as compared to the conventional rate through the promotion of osteoblast formation therein and thus, the reconstruction of skull defects and the orthopedic treatment of bone-grafted sites are accelerated and a quick recovery time can be sought.

(Void Volume)

The average pore diameter and void fraction of compressed fiber structural material 1 can be obtained by the pore distribution measurement in accordance with the mercury penetration method. The mercury penetration method is a method in which mercury is penetrated into the pores in samples such as porous particles and the like while applying pressure thereon and then the information on specific surface area and pore diameter distribution, etc. is obtained from the relationship between the applied pressure and the amount of mercury which has penetrated therein. In particular, first, after evacuating a container containing the samples, such container is filled with mercury. Mercury has a strong surface tension and thus it does not penetrate into the pores at the sample surface as it is. However, when the pressure is gradually increased by applying pressure to the mercury, it starts to slowly penetrate into the pores in order from the pores with a larger diameter to the pores with a smaller diameter. By detecting the change in mercury liquid level (i.e. the amount of mercury penetration into the pores) while continuously increasing the pressure, a mercury penetration curve can be obtained, representing the relationship between the pressure applied to the mercury and the amount of mercury penetration.

Here, when it is assumed that the shape of the pores is cylindrical and when the radius thereof is denoted by "r" (nm), the surface tension of mercury is denoted by "δ" (dyn/cm) and the contact angle is denoted by "θ" (°), the magnitude of the force in the direction of pushing the mercury out of the pores is represented by $-2\pi r\delta (\cos \theta)$ (when θ>90°, the value would be positive). In addition, the magnitude of the force in the direction of pushing the mercury into the pores under pressure P is represented by $\pi r^2 P$ and thus, based on the balance between these forces, mathematical formulae (1) and (2) below are derived. In the case of mercury, a surface tension δ of approximately 480 dyn/cm and a contact angle θ of approximately 140° are the values commonly used. When these values are used, the radius r (nm) of the pores into which the mercury will penetrate under pressure P is represented by mathematical formula (3) below.

$$-2\pi r\delta(\cos \theta) = \pi r^2 P \qquad (1)$$

$$Pr = -2\delta(\cos \theta) \qquad (2)$$

$$r(\text{nm}) = (7.5 \times 10^8)/P \qquad (3)$$

Namely, since there is a correlation between pressure P applied to the mercury and radius r of the pores into which the mercury will penetrate, based on the obtained mercury penetration curve, a pore distribution curve representing the relationship between the radius size of the pores in the sample and the volume thereof can be obtained. For example, when pressure P is varied from 0.01 MPa to 500 MPa, measurements can be performed on pores having a diameter in the range of approximately 100 μm-4 nm. It should be noted that the approximate limits of measuring the pore radius by the mercury penetration method are approximately 2 nm or more for the lower limit and approximately 200 μm or less for the upper limit and thus, such method is more suitable for pore distribution analysis of pores having their radius in a relatively wide range, as compared to the nitrogen adsorption method.

The measurement in accordance with the mercury penetration method can be performed using an device such as a mercury porosimeter or the like. Specific examples of a mercury porosimeter include Mircometrics' AutoPore and Quantachrome's PoreMaster, etc.

An average pore diameter of the measured compressed fiber structural material 1 is in the range of 60-100 μm inclusive and a void fraction thereof is in the range of 25-50% inclusive.

Compressed fiber structural material 1 having pores with characteristics within the above-described ranges possesses voids with dimensions that can help osteoblast to form. Compressed fiber structural material 1 has such voids at a specific proportion and thus, the generation of osteoblast in such voids easily occurs and the rate of osteoblast generation can be increased by double or more as compared to the conventional rate. As a result, the reconstruction of skull defects and the orthopedic treatment of bone-grafted sites are accelerated and a quick recovery time can be sought. In addition, the strength of compressed fiber structural material 1 having an average pore diameter and void fraction in the above-described ranges is not too strong and compressed fiber structural material 1 also has flexibility. Accordingly, compressed fiber structural material 1 has desired mechanical characteristics matched to the bone strength. As a result, even when a difference in strength exists, depending on the sites to be treated, or when a difference in bone strength from that of adult males exists for children, females or and the elderly, compressed fiber structural material 1 still has mechanical characteristics useable for the respective sites and people and thus, it is extremely effective.

When the average pore diameter is 60 μm or less and the void fraction is 25% or less, the volume of voids required for osteoblast generation is small and that thus, sufficient osteoblast generation may not occur. In addition, the strength may become high due to an increase in bulk density and the strength value may depart from the strength value of in vivo bone. On the other hand, when the average pore diameter exceeds 100 μm and the void fraction also exceeds 50%, the volume of voids having the above-described diameter would increase. This is sufficient for the osteoblast generation; however, the strength may be reduced or the brittleness may be increased due to a decrease in the bulk density.

Compressed fiber structural material 1 can be evaluated in terms of a bulk density. The bulk density of compressed fiber structural material 1 provided with the preferable volume of voids as described above is preferably 0.5-1 times the specific weight of biocompatible fiber 14, which is the raw material thereof. For example, when biocompatible fiber 14 is a titanium fiber having a specific weight of 4.5, the bulk density of compressed fiber structural material 1 produced with such titanium fiber is preferably in the range of 2.2-4.5 g/cm$^3$. The bulk density in this range can be controlled by the cold pressing/shearing. Compressed fiber structural material 1 having such bulk density is a structural material having predetermined voids in the interior thereof and thus, the strength thereof is not too strong and it also has flexibility. Accordingly, compressed fiber structural material 1 has desired mechanical characteristics matched to the bone strength. This bulk density was determined by dividing the mass of the measured test piece by the volume thereof. In particular, for the test piece, for example, a piece cut out into a square having 5 mm sides, by wire-cutting discharge was used.

When the bulk density of compressed fiber structural material 1 is 2.2 g/cm$^3$ or less, the strength may be reduced or the brittleness may be increased due to a decrease in the bulk density. On the other hand, when the bulk density of compressed fiber structural material 1 exceeds 4.5 g/cm$^3$, the strength becomes high and the strength value may depart from the strength value of in vivo bone.

It should be noted that the average pore diameter and void fraction measured by the mercury penetration method can be controlled to within the above-described ranges by the cold pressing/shearing using various parameters set as described above. In particular, by controlling the type, size (average diameter and aspect ratio) and fill amount of biocompatible fiber 14 and compressive stress P1, shearing stress P2 and shearing stroke length d at the time of cold pressing/shearing, the average pore diameter and void fraction can be controlled to within the above-described ranges.

As described above, the cold pressing/shearing has an advantage to the effect that the void structure (i.e. the average pore diameter and the void fraction) and the mechanical characteristics of compressed fiber structural material 1, which are to be estimated by the bulk density and the mercury penetration amount, can be arbitrarily set by adjusting the processing conditions such as compressive stress P1, shearing stress P2 and the shearing stroke length, etc. and also by adjusting the fill amount and the like of biocompatible fiber 14 and thus, compressed fiber structural material 1 having its strength matched to the strength of the target in vivo bone can be produced.

As described above, according to the method for producing compressed fiber structural material 1 according to the present invention, biocompatible fiber 14 having an average diameter and an aspect ratio within the above-described ranges is used and molding is performed such that the average pore diameter and the void fraction are within the above-described ranges through the cold pressing/shearing. Thus, produced compressed fiber structural material 1 has high biocompatibility, which is possessed by the fiber itself, and is provided with voids which can help osteoblast to form therein, and it can further be used as a biomaterial having desired mechanical characteristics matched to the bone strength. As a result, even when a difference in strength exists, depending on the sites to be treated, compressed fiber structural material 1 having mechanical characteristics close to those of in vivo bone can still be easily be produced. In addition, since the obtained compressed fiber structural material is provided with voids exhibiting the average pore diameter and void fraction in the above-described ranges, such voids allow the rate of osteoblast generation to be increased by double or more as compared to the conventional rate, and thus, the reconstruction of skull defects and the orthopedic treatment of bone-grafted sites are accelerated and a quick recovery time can be sought.

In addition, the cold pressing/shearing applied in the present invention can vary the mechanical characteristics, such as the elasticity and flexibility, of obtained compressed fiber structural material 1 by arbitrarily setting the compressive stress, the shearing stroke length and the shearing velocity, etc. and thus, even when a difference in strength exists, depending on the sites to be treated, or when a difference in bone strength from that of adult males exists for children, females or the elderly, it is still possible to easily produce compressed fiber structural material 1 having mechanical characteristics useable for the respective sites and people, and thus, the cold pressing/shearing applied in the present invention is an extremely effective means. Examples of such characteristics include, for example, strength close to that of the patient's bone and any strength that allows the prevention of a weak site from being broken in cases where a strong site and a weak site are combined together and where the weak site is prone to breakage since the stress is concentrated thereon.

EXAMPLES

The present invention will now be specifically described by various experiments below.

[Production of Compressed Fiber Structure Material]

Fibrous titanium (available from Nikko Techno) having an average diameter of approximately 20 μm and made of pure titanium having a purity of 99.52% (Class I) was used as biocompatible fiber 14. The titanium fiber was produced by a coil material cutting method in which a titanium thin plate having a thickness of 20 μm was wound in a coil form and an end face thereof was cut so as to obtain the titanium fiber. This biocompatible fiber 14 was molded in cold pressing/shearing device 20 illustrated in FIG. 3 so as to obtain compressed fiber structural material 1.

In particular, first, on top of fixed plate 10 illustrated in FIG. 2(A), penetrated mold 12 provided with penetration hole 13 having the dimensions of 15 mm (height)×40 mm×10 mm, was installed (see FIG. 2(B)) and biocompatible fiber 14 was filled in such penetrated mold 12 (see FIG. 2(C)). Subsequently, penetrated mold 12 was removed (see FIG. 2(D)) and after installing fixed plate 10 onto device 20, moving plate 16 was placed on biocompatible fiber 14 (see FIG. 2(E)). Subsequently, device 20 was activated to load biocompatible fiber 14 with compressive stress P1 (see FIG. 2(F)). Compressive stress P1 was measured by means of load cell 21 installed at the upper portion of the device. Subsequently, while loading with compressive stress P1, moving plate 16 was moved in a lateral direction so as to load biocompatible fiber 14 with shearing stress P2 and then compressed fiber structural material 1 illustrated in FIG. 5 was produced (FIGS. 2(G) and 2(H)). Shearing stroke length d was measured using displacement gauge 25 and shearing stress P2 was measured by a four-active gauge method (a perpendicular alignment method) using four strain gauges 23 (available from Kyowa Electronic Instruments Co., Ltd., model number: KGF-2-120-C1-11) attached to a cylinder arranged between a screw and moving plate 16. Obtained compressed fiber structural material 1 had the dimensions of 0.5 mm (thickness)×43 mm×13 mm

[Osteoblast Culture Experiment]

In order to examine the behavior of osteoblast in produced compressed fiber structural material 1, an osteoblast culture experiment was conducted at the surface of compressed fiber structural material 1. Compressed fiber structural material 1 used for the culture was obtained through the production procedure described above with the production conditions set forth in Table 1.

TABLE 1

| | |
|---|---|
| mass of biocompatible fiber (g) | 0.5 |
| fiber length (μm) | 10000 |
| aspect ratio | 500 |
| compressive stress (MPa) | 1000 |
| shearing velocity (mm/minute) | 1.0 |
| shearing distance (mm) | 1.0 |
| shearing strain | 3.33 |

In the osteoblast culture experiment, obtained compressed fiber structural material 1 was processed into a disc form having a diameter of 10 mm, and 3,500 cells of the respective osteoblast, chondrocyte and fibroblast were dispersed on the processed sample surface and the culture was carried out for 168 hours (one week). After the culture, the number of cells was calculated by a DAPI staining method. The result thereof is set forth in Table 2. Based on Table 2, it can be seen that the number of the respective cells at the sample surface did not decrease but rather increased over time. Out of the respective cells, the number of osteoblast cells increased the most. Based on this result, it became clear that produced compressed fiber structural material 1 can be used as a biomaterial.

TABLE 2

| | number of cells (per unit/m$^2$) | | | |
|---|---|---|---|---|
| | in 2 hours | in 24 hours | in 72 hours | in 168 hours |
| osteoblast | 5700 | 6800 | 8300 | 10400 |
| chondrocyte | 3800 | 4400 | 5000 | 6000 |
| Fibroblast | 3400 | 4000 | 4200 | 4800 |

Figure 6:
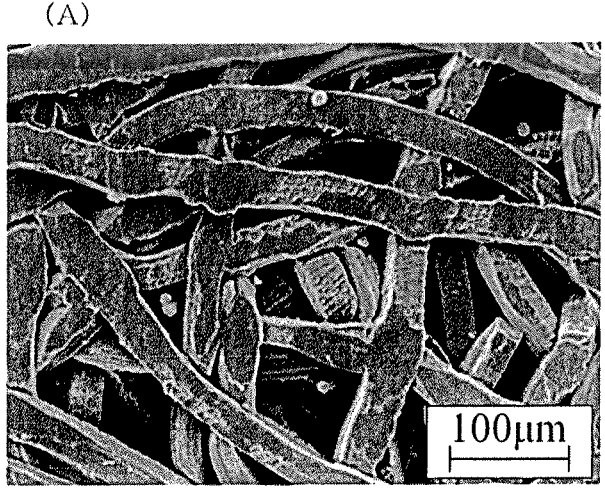
FIG. 6 shows SEM images of a sample surface after 24 hours have elapsed from the beginning of culture.
Figure 6:
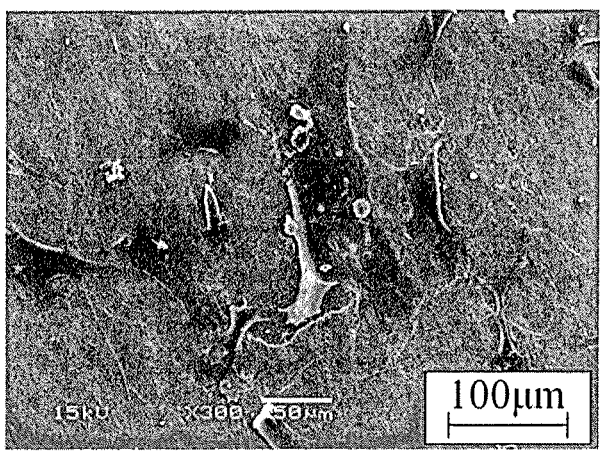

FIG. 6 shows SEM images of the sample surface after 24 hours have elapsed from the beginning of the culture. As shown in FIG. 6(A), at the section of the sample surface where the fibrous form of the titanium fiber remained, the number of osteoblast cells increased by a large amount and as shown in FIG. 6(B), at the flat section where the fibrous form did not remain, the number of osteoblast cells did not increase by a large amount. Through the osteoblast culture experiment, an increase in the number of osteoblast cells was observed at the surface of compressed fiber structural material 1 produced by the cold pressing/shearing method. In addition, when the surface roughness of compressed fiber structural material 1 was uniform, the number of osteoblast cells also increased in a uniform manner.

[Influence of Aspect Ratio]

Compressed fiber structural materials 1 were produced using titanium fibers having different aspect ratios and their influence on the mechanical characteristics was considered. As for the mechanical characteristics, surface observation, surface roughness measurement, tensile testing, bending testing and density measurement were conducted.

(Molding Conditions and Appearance Diagram of Compressed Fiber Structural Material)

Figure 7:
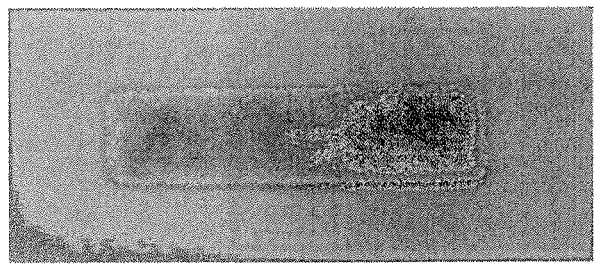
FIG. 7 shows photographs of the appearance of the compressed fiber structural material.
Figure 7:
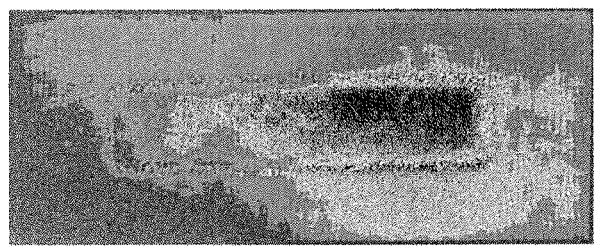
Figure 7:
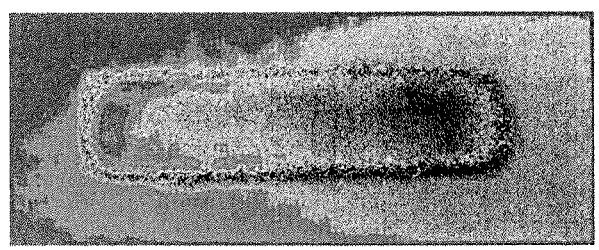
Figure 7:
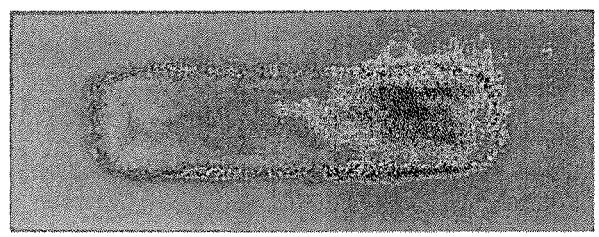

Table 3 lists the production conditions of produced compressed fiber structural materials 1. FIG. 7 shows photographs of the appearance of obtained compressed fiber structural materials 1. From FIG. 7, it can be seen that the external dimensions of compressed fiber structural materials 1 increased in association with an increase in aspect ratio (AR). It is considered that this is due to the fact that, when the aspect ratio is large, the bulk of the titanium fiber at the time of cold pressing/shearing is large, and thus, when compression load P1 was loaded, it protruded outside. From FIG. 7, it can be seen that the protruding portion still maintained the fibrous form to such an extent that it could be seen by the naked eyes and it differed from the central portion which is uniformly in a plate form. The size of the surface which is uniformly molded in a plate form did not differ depending on the aspect ratio and it was approximately 10 mm×40 mm, in the form of the penetration hole in the penetrated mold used for molding.

TABLE 3

| | | | | |
|---|---|---|---|---|
| mass of biocompatible fiber (g) | | 1.0 | | |
| fiber length (μm) | 500 | 1000 | 5000 | 10000 |
| aspect ratio | 25 | 100 | 250 | 500 |
| compressive stress (MPa) | | 1000 | | |
| shearing velocity (mm/minute) | | 1.0 | | |
| shearing distance (mm) | | 0.4 | | |
| shearing strain | | 0.67 | | |

Figure 8:
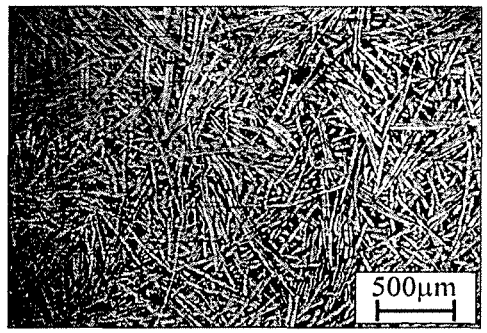
FIG. 8 shows optical microscope photographs of the surface of the compressed fiber structural material molded with biocompatible fibers having different aspect ratios.
Figure 8:
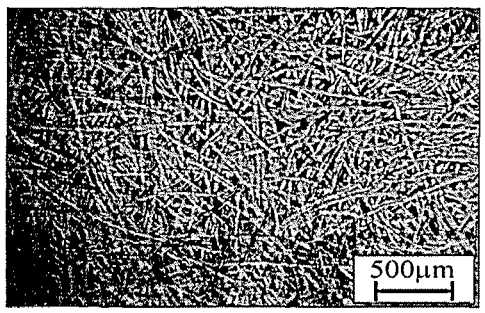
Figure 8:
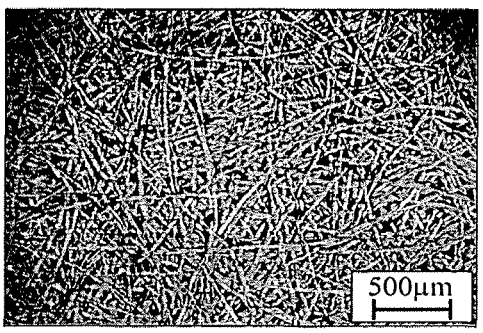
Figure 8:
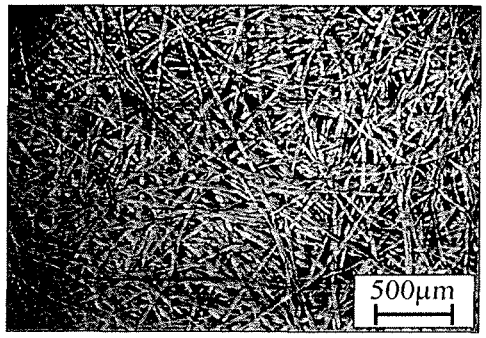

FIG. 8 shows optical microscope photographs of the surface of compressed fiber structural materials 1 obtained with the conditions listed in Table 3. From FIG. 8, it can be seen that compressed fiber structural materials 1 had a surface still maintaining the fibrous form. In addition, it can also be seen that the titanium fiber was not ruptured by the cold pressing/shearing and the fiber that can be observed at the surface of compressed fiber structural materials 1 was elongated in association with the increase in aspect ratio. When the aspect ratio AR is 25, the fiber length is 500 μm and thus, the directional property of the irregularities is the smallest and thus, it is considered that osteoblast will increase in a more uniform manner.

(Surface Roughness)

In order to evaluate the surface texture of compressed fiber structural materials 1 shown in FIG. 8, the surface roughness measurement was conducted. An ultradeep profile measuring microscope (available from Keyence, model number: VK-8500) was used for the measurement, and the measurement was conducted in both the shearing direction and the direction perpendicular thereto, with the measurement conditions being: objective lens (10×), measurement pitch (0.05 mm) and reference length (1000 μm).

Both values of the arithmetic average roughness Ra in the shearing direction and in the direction perpendicular thereto when the aspect ratio was 25 were approximately 8.8 μm, both values of the arithmetic average roughness Ra in the shearing direction and in the direction perpendicular thereto when the aspect ratio was 100 were approximately 5.6 μm, both values of the arithmetic average roughness Ra in the shearing direction and in the direction perpendicular thereto when the aspect ratio was 250 were approximately 5 μm, and both values of the arithmetic average roughness Ra in the shearing direction and in the direction perpendicular thereto when the aspect ratio was 500 were approximately 5.7 μm. In addition, as compared with the compressed fiber structural fiber used in the osteoblast culture experiment, the produced compressed fiber structural fiber has a smaller error in the arithmetic average roughness Ra and thus, a surface having a uniform roughness was obtained. In addition, very little difference could be seen in the arithmetic average roughness Ra between the shearing direction and the direction perpendicular thereto and the irregularities of the compressed fiber structural material were isotropic. Further, the largest arithmetic average roughness Ra of the compressed fiber structural material was obtained when the aspect ratio AR was 25 and thus, an improvement in the increased number of osteoblast cells in the osteoblast culture experiment could be expected. It should be noted that the arithmetic average roughness Ra was evaluated with reference to JISB 0601-1994.

(Cross-Sectional Form)

Figure 9:
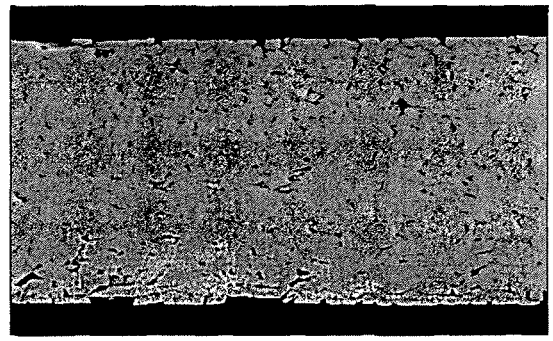
FIG. 9 shows SEM photographs of the cross section of the compressed fiber structural material molded with biocompatible fibers having different aspect ratios.
Figure 9:
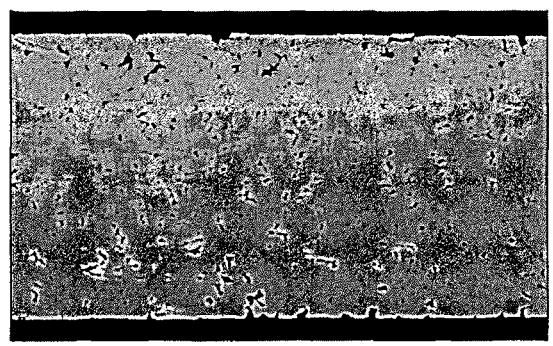
Figure 9:
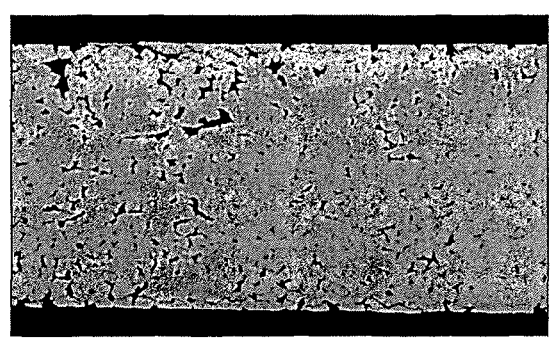
Figure 9:
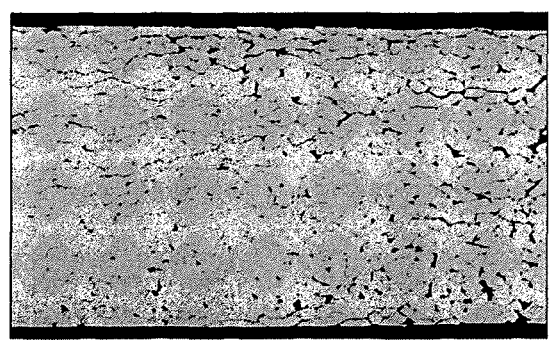

FIG. 9 shows SEM photographs of the cross section of the compressed fiber structural material. From FIG. 9, it can be observed that the compressed fiber structural material has voids in the interior thereof, the fibers do not bind to each other and the fibers are intertwined with each other. The reason why there was no binding between the fibers is because a low compressing load and a small shearing distance are sufficient for obtaining the compressed fiber structural material of the present invention, which has a predetermined amount of voids.

(Tension Test)

Figure 10:
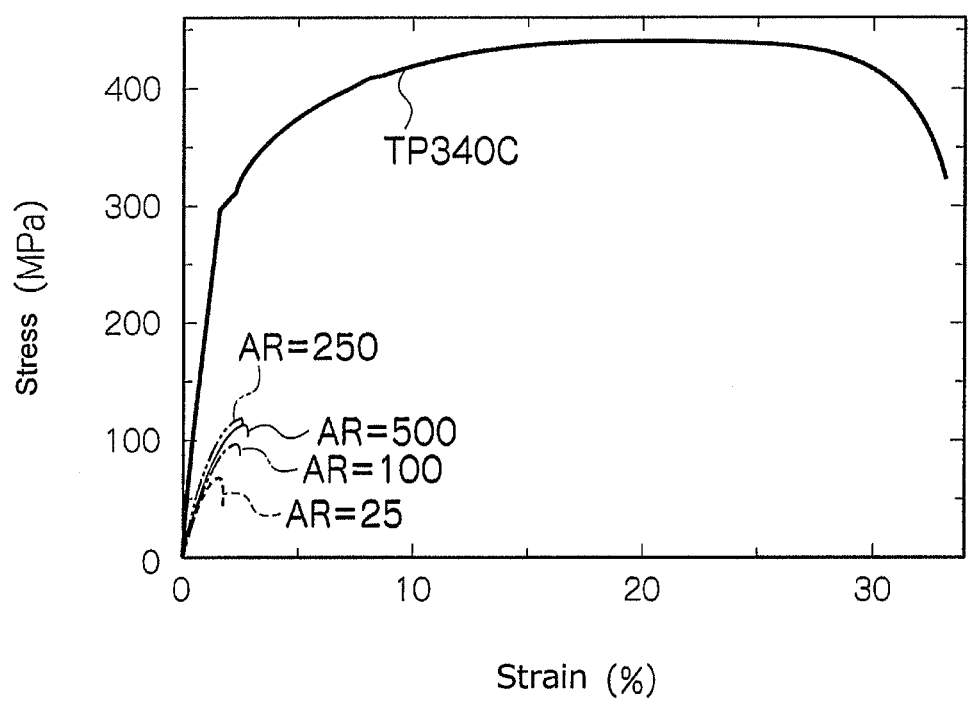
FIG. 10 is a diagram illustrating stress-strain curves obtained through tests.

The tension test was conducted, with reference to the former JIS Z 2201, using a compact desk-top tester (available from Shimazu Corporation, model number: EZ-L-500N) with a testing rate of 0.5 mm/min at room temperature (25° C.). The test piece was made in accordance with the No. 7 test piece. A strain gauge (available from Kyowa Electronic Instruments Co., Ltd., model number: KGF-2-120-C1-11) was attached to a parallel portion of the test piece and the strain at the time of testing was measured and the measurement was used to derive a Young's modulus. FIG. 10 is a diagram illustrating stress-strain curves obtained through such testing. From FIG. 10, it can be seen that the tensile strength and the stretch of the compressed fiber structural material obtained by the cold pressing/shearing method increased in association with the increase in aspect ratio; however, the tensile strength did not increase when the aspect ratio AR was 250 or more.

Table 4 shows the Young's modulus and the tensile strength resulting from the compressed fiber structural material produced with fibers having different aspect ratios. Table 4 also includes values for a pure titanium rolled material (TP 340 C) having a thickness of 0.5 mm and for compact bone for the comparison purposes. As shown in Table 4, the Young's modulus of the produced compressed fiber structural material exhibited some changes in accordance with a change in aspect ratio; however, it eventually assumed a constant value of approximately 20-30 GPa. It should be noted that since the Young's modulus of the pure titanium rolled material is 98.6 GPa and the Young's modulus of the compact bone is 10-17 GPa, it can be seen that that the Young's modulus of the compressed fiber structural material was approximately one-third (⅓) of that of the pure titanium rolled material and was approximately 1.7-times that of the compact bone. On the other hand, as shown in Table 4, the tensile strength of the pure titanium rolled material is 438 MPa and the tensile strength of the compact bone is 88-114 MPa, and thus, it can be seen that that the value of the tensile strength varied from a value less than that of the compact bone (i.e. approximately 70 MPa) to a comparable value (i.e. approximately 100 MPa) and then to a value over than that of the compact bone (i.e. approximately 120 MPa) in association with the increase in aspect ratio.

TABLE 4

|  | aspect ratio | | | |
| --- | --- | --- | --- | --- |
|  | 25 | 100 | 250 | 500 |
| Young's modulus (GPa) | 20 | 30 | 25 | 22 |
| tensile strength (MPa) | 70 | 100 | 120 | 115 |

(Three-Point Bending Test)

Figure 11:
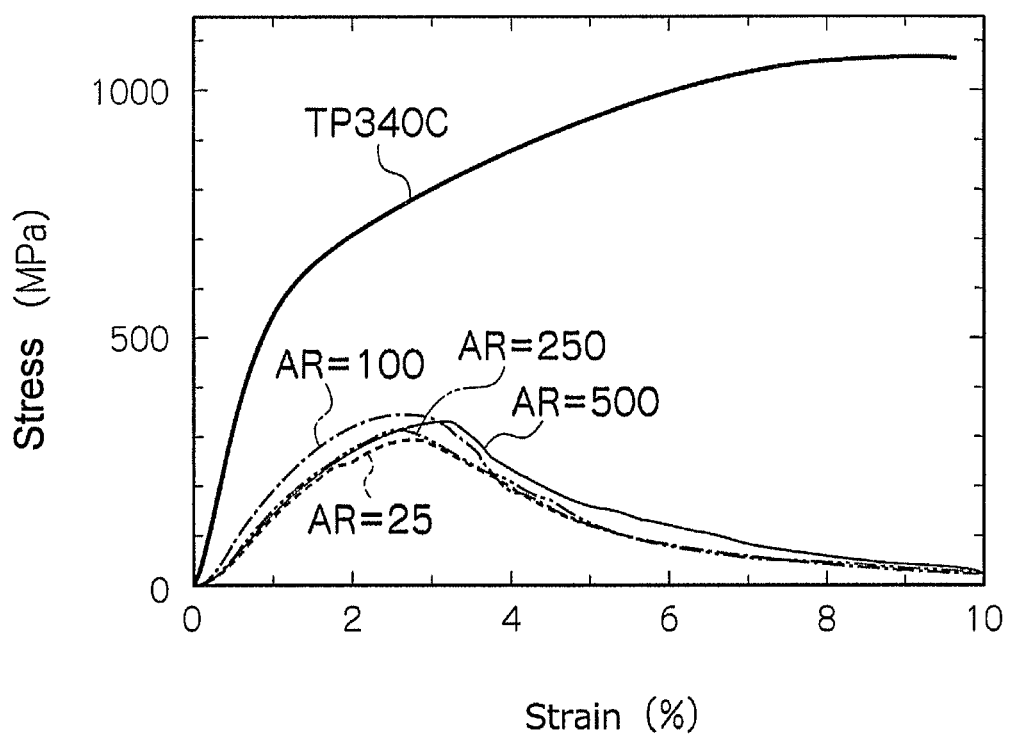
FIG. 11 is a diagram illustrating stress-strain curves obtained through tests.

The three-point bending test was conducted, with reference to JIS K 7171, using a compact desk-top tester (available from Shimazu Corporation, model number: EZ-L-500N) with a distance between fulcrums of 6.0 mm and a testing rate of 0.5 mm/min at room temperature (25° C.). A strain gauge (available from Kyowa Electronic Instruments Co., Ltd., model number: KGF-02-120-C1-11) was attached to a central portion of the produced test piece and the strain at the time of testing was measured and the measurement was used to derive a bending elastic modulus. FIG. 11 is a diagram illustrating stress-strain curves obtained through such testing. It should be noted that formula (4) below shows the calculation formula of stress σ and that formula (5) below shows the calculation formula of bending strain ε used for creating the diagram illustrating the stress-strain curves. In formula (4), "σ" denotes a bending stress (MPa), "F" denotes a test force (N), "L" denotes a distance (mm) between fulcrums, "b" denotes a width (mm) of the test piece, and "t" denotes a thickness (mm) of the test piece. In formula (5), "ε" denotes a bending strain (%), "s" denotes a deflection (mm), "t" denotes a thickness (mm) of the test piece and "L" denotes a distance (mm) between fulcrums.

$$\sigma(MPa) = 3\ FL/2\ bt^2 \quad (4)$$

$$\epsilon(\%) = 600\ st/L^2 \quad (5)$$

FIG. 11 also includes the test results of the pure titanium rolled material (TP 340 C) having a thickness t of 0.5 mm for the comparison purposes. From FIG. 11, it can be seen that all of the compressed fiber structural materials obtained by the cold pressing/shearing method, even when they made use of biocompatible fibers having different aspect ratios, exhibited almost identical behaviors but exhibited a low bending elastic modulus and low bending strength as compared to those of the pure titanium rolled material. Table 5 shows the bending elastic modulus and the bending strength resulting from the compressed fiber structural material produced with fibers having different aspect ratios. Table 5 also includes values for a pure titanium rolled material (TP 34 C) having a thickness of 0.5 mm and for compact bone for the comparison purposes.

Both the bending elastic modulus and the bending strength exhibited some changes in accordance with a change in aspect ratio; however, they eventually assumed a constant value of approximately 30 GPa and 310 MPa, respectively. It should be noted that since the bending elastic modulus of the pure titanium rolled material is 99.7 GPa and the bending elastic modulus of the compact bone is 10-17 GPa, it can be seen that the bending elastic modulus of the compressed fiber structural material was approximately one-third (⅓) of that of the pure titanium rolled material and was approximately 1.7-times that of the compact bone. On the other hand, since the bending strength of the pure titanium rolled material is 1070 MPa and the bending strength of the compact bone is 100-200 MPa, it can be seen that the bending strength of the compressed fiber structural material obtained by the cold pressing/shearing method was approximately one-third (⅓) of that of the pure titanium rolled material and was approximately 1.5-3-times that of the compact bone.

TABLE 5

|  | aspect ratio | | | |
|---|---|---|---|---|
|  | 25 | 100 | 250 | 500 |
| bending elastic modulus (GPa) | 30 | 32 | 28 | 29 |
| bending strength (MPa) | 280 | 320 | 310 | 320 |

(Bulk Density)

The measurements of the bulk density were determined by dividing the mass of the measured test piece by the volume thereof. For the test piece, for example, a piece cut out from the obtained compressed fiber structural material into a square having 5 mm sides by wire-cutting discharge was used. Pure titanium rolled material having a thickness of 0.5 mm was also measured for the comparison purposes. Accordingly, the bulk density of the pure titanium rolled material was determined to be 4.35 g/cm$^3$ and the bulk density of the produced compressed fiber structural material was determined, regardless of the aspect ratio, to be constant around 3.7 g/cm$^3$, which was approximately 0.85-times that of the pure titanium rolled material.

(Void Fraction Measurement)

Since the average pore diameter and the void fraction of the compressed fiber structural material have an influence on the ingrowth of osteoblast, measurement of the average pore diameter and void fraction was conducted by a mercury penetration test. Through the mercury penetration test, the amount of mercury which penetrates into the voids in the sample in response to a penetration pressure can be measured. By applying the value of the penetration pressure of the mercury obtained as test result to Washburn's formula indicated in formula (6), the radius of a pore can be determined.

$$Pc = -(2\Phi_m \cos\theta_m)/r \quad (6)$$

Figure 12:
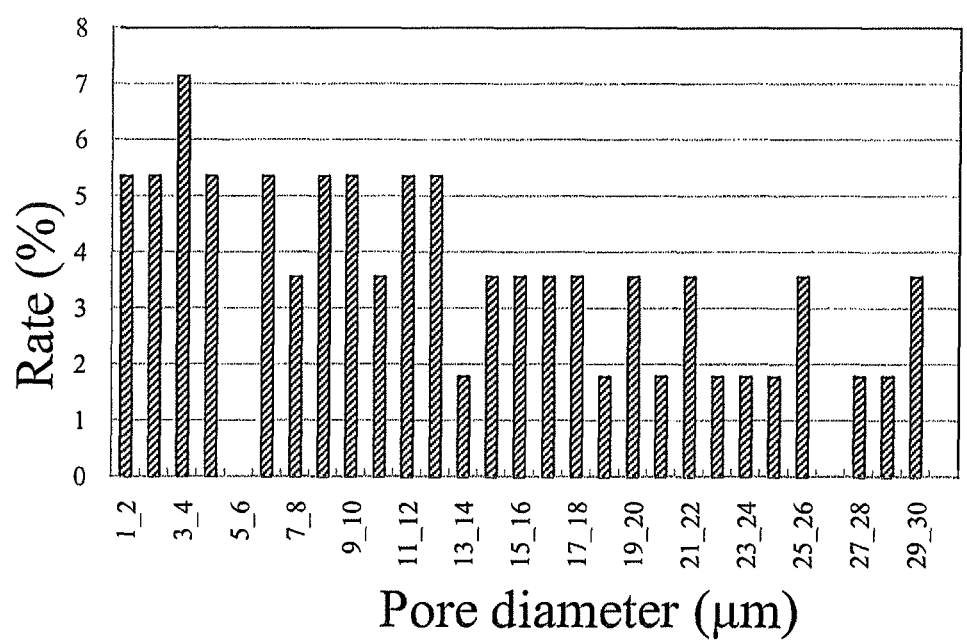
FIG. 12 is a graph illustrating the relationship between void fractions and pore diameters derived from the results of a mercury penetration test of a compressed fiber structural material.

In formula (6), "Pc" corresponds to the penetration pressure in the mercury penetration test. The reference "r" denotes a radius of a void, which is modeled as a cylindrical form, into which mercury can penetrate in response to penetration pressure Pc, "$\theta_m$" denotes an angle of contact between the mercury and the interface of the cylindrical void and "$\Phi_m$" denotes interface energy (surface tension) of the mercury. By making use of formula (6), the penetration pressure of the test result was converted into a radius of a cylindrical void and the void distribution was determined by interpreting that the amount of mercury penetration was a void capacity directly corresponding to the cylindrical void. It should be noted that, here, the measurement was made up to a diameter of 30 μm. FIG. 12 is a graph illustrating the relationship between the void fraction and the pore diameter derived from the result of the mercury penetration test on the compressed fiber structural material. From FIG. 12, it can be seen that the compressed fiber structural material has pores in the interior thereof and, further, that the pores having a diameter of at most 30 μm existed.

Figure 13:
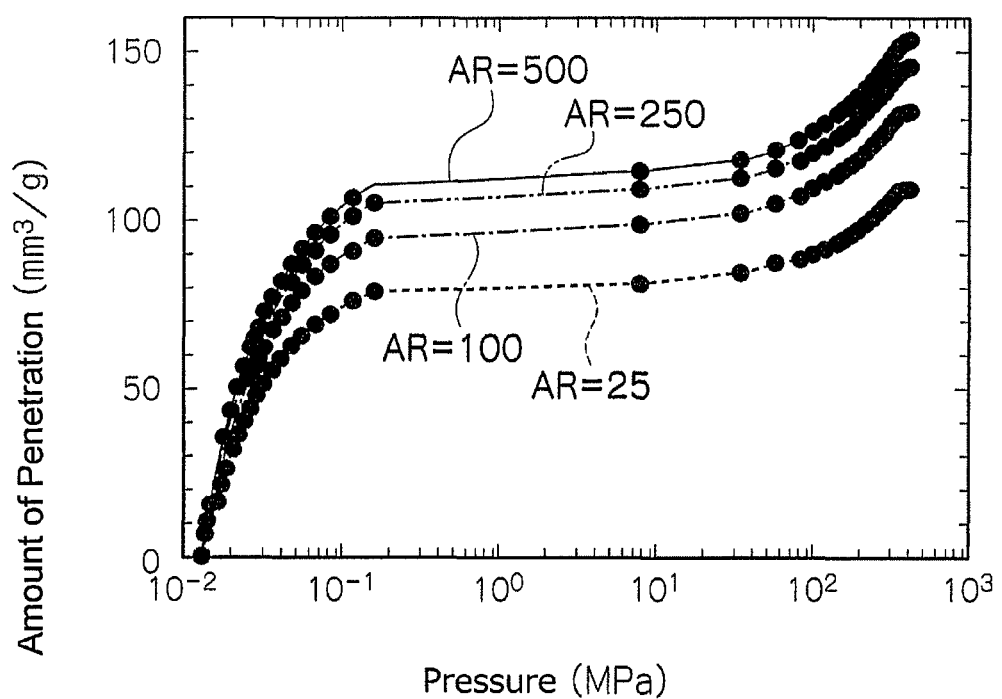
FIG. 13 is a graph illustrating mercury penetration curves representing the relationship between the pressure applied to mercury and the amount of mercury penetration.

FIG. 13 is a graph illustrating mercury penetration curves representing the relationship between the pressure applied to the mercury and the amount of mercury penetration. From FIG. 13, it can be seen that when the pressure applied to the mercury was increased, the mercury penetration amount increased until approximately 0.2 MPa was reached. However, it exhibited substantially the same and constant value between approximately 2.0 MPa and 100 MPa. Thereafter, at pressure values over 100 MPa, the mercury penetration amount started to increase again. Compressed fiber structural materials making use of a biocompatible fiber having a larger aspect ratio exhibited a higher mercury penetration amount. For example, for a given area from approximately 0.2 MPa to 100 MPa, when the aspect ratio was 25, the mercury penetration amount was approximately 77 mm$^3$/g, when the aspect ratio was 100, the mercury penetration amount was approximately 90 mm$^3$/g, and when the aspect ratio was 500, the mercury penetration amount was approximately 120 mm$^3$/g.

Table 6 shows the average pore diameter and the void fraction of the respective compressed fiber structural materials molded with biocompatible fibers having different aspect ratios, which are obtained and result from the mercury penetration curves in FIG. 13. Based on these results, it can be observed that, for any given aspect ratio, the average pore diameter in the compressed fiber structural material is in the range of 60-100 μm inclusive and the void fraction in the compressed fiber structural material is in the range of 25-50% inclusive. It should be noted that the void fraction had a tendency to increase in association with the increase in aspect ratio. Table 6 also includes the total mercury penetration amount and the total surface area. Based on these results, it can be seen that, in association with the increase in aspect ratio, both the total mercury penetration amount and the total surface area have a tendency to increase.

TABLE 6

|  | aspect ratio | | | |
|---|---|---|---|---|
|  | 25 | 100 | 250 | 500 |
| average pore diameter (μm) | 88 | 88 | 70 | 88 |
| void fraction (%) | 32 | 37 | 39 | 40 |
| total mercury penetration amount (mm$^3$/g) | 110 | 130 | 146 | 153 |
| total surface area (mm$^3$/g) | 12 | 16 | 17 | 18 |

[Operational Advantages]

As described above, in the present invention, after molding a biocompatible fabric such as a titanium fiber into a lamellar form using a cold pressing/shearing method, an observation was made with respect to the behavior of osteoblast on the compressed fiber structural material and the influence on the mechanical characteristics of a change in aspect ratio of the titanium fiber at the time of molding. Then, the following findings became clear:

(1) As a consequence of conducting an osteoblast culture experiment, it was observed that the number of osteoblast cells increased over time at the surface of the compressed fiber structural material. In addition, the behavior of the osteoblast differed between the section where a fibrous form still remained and the flat section where no fibrous form remained, and the number of osteoblast cells increased more in the sections where fibrous forms still remained;

(2) It can be seen that the surface of the compressed fiber structural materials molded by varying the aspect ratio was more uniform and had isotropic irregularities as compared to the compressed fiber structural materials used for the osteoblast culture experiment;

(3) It can be seen that the tensile strength increased in association with the increase in aspect ratio and that it did not change when the aspect ratio AR was 250 or more; and It can be seen that the bending elastic modulus and the bending strength were approximately one-third (⅓) of those of a pure titanium rolled material and approximately 1.7-times those of compact bone.

Based on the above, it can be observed that the number of osteoblast on the titanium fabric lamella produced using the cold pressing/shearing method increased over time and that such lamella had mechanical characteristics close to those of in vivo bone as compared to those of a rolled material. In particular, the mechanical characteristics of the compression fiber structural material, the titanium fiber thereof has an aspect ratio of 25, were the closest to those of in vivo bone and thus, such compression fiber structural material is a promising material as a biomaterial for fixing bone-grafted sites. In particular, the compressed fiber structural material has an advantage to the effect that it can be easily wound to the bone by hand because of its flexibility and thus, treatment can be provided more easily. Moreover, it can also be observed that, since the rate of osteoblast generation was twice as fast as that of the conventional biomaterials, the time required for healing was reduced by half.

In the cold pressing/shearing method applied in the present invention, the biocompatible fibers such as titanium fibers were bonded to each other by superimposing them onto each other and conducting the method. Thus, it was easy to vary the thickness thereof. The produced lamellar compressed fiber structural material may be required to be of a particular strength, depending on the application, or may be required to be of a particular strength close to that of the bone. Such compressed fiber structural material has an advantage to the effect that it can easily respond to the respective demands.

[Production of Composite Compressed Fiber Structural Material]

The following provides a specific example of compressed fiber structural material 1 in which a titanium fiber and a magnesium powder are compounded.

(Raw Material for Compounding)

Figure 14:
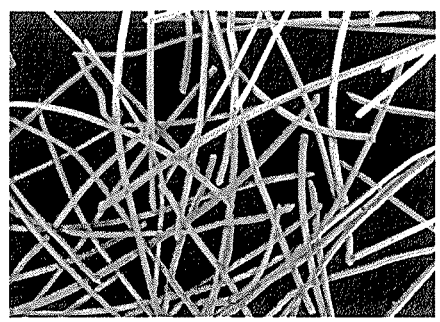
FIG. 14 is a schematic cross-sectional diagram illustrating an example of a compressed fiber structural material (C) obtained by compounding a titanium fiber (A) and magnesium powder (B).
Figure 14:
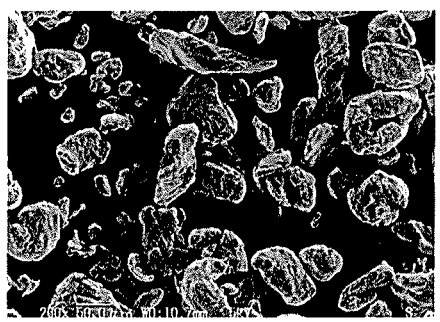
Figure 14:
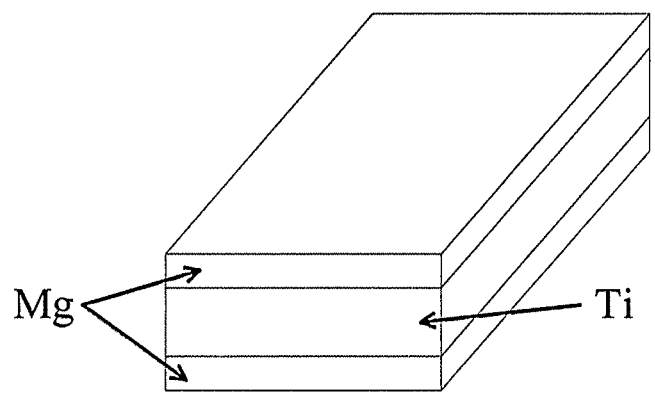

For a titanium fiber, fibrous titanium (available from Nikko Techno) having an average diameter of approximately 20 μm and made of pure titanium having a purity of 99.52% (Class I) was used (see FIG. 14(A)). The titanium fiber was produced by a coil material cutting method in which a titanium thin plate having a thickness of 20 μm was wound in a coil form and an end face thereof was cut to obtain the titanium fiber. For a titanium powder, powder titanium (available from Kantometal Co., Ltd.) having a purity of 99.6% and an average particle diameter of 106 μm was used (see FIG. 14(B)).

(Cold Pressing/Shearing)

A titanium fiber and a magnesium powder were compounded together. First, the titanium fiber was molded with cold pressing/shearing device 20 illustrated in FIG. 3 to obtain a primary compressed compact of the titanium fiber. In particular, first, on top of fixed plate 10 illustrated in FIG. 2(A), penetrated mold 12 provided with penetration hole 13 having the dimensions of 15 mm (height)×40 mm×10 mm, was installed (see FIG. 2(B)) and the titanium fiber was filled in such penetrated mold 12 (see FIG. 2(C)). Subsequently, penetrated mold 12 was removed (see FIG. 2(D)) and after installing fixed plate 10 onto device 20, moving plate 16 was placed on the titanium fiber (see FIG. 2(E)). Subsequently, device 20 was activated to load the titanium fiber with compressive stress P1 (compressive stress: 1250 MPa and compression load: 500 kN) (see FIG. 2(F)). Compressive stress P1 was measured by means of load cell 21 installed at the upper portion of the device. Subsequently, while loading with compressive stress P1, moving plate 16 was moved in a lateral direction (shearing velocity: 1 mm/min and shearing distance: 0.25 mm) to load the titanium fiber with shearing stress P2 and then the primary compressed compact of the titanium fiber was produced (FIGS. 2(G) and 2(H)). Shearing stroke length d was measured using displacement gauge 25 and shearing stress P2 was measured by a four-active gauge method (a perpendicular alignment method) using four strain gauges 23 (available from Kyowa Electronic Instruments Co., Ltd., model number: KGF-2-120-C1-11) attached to a cylinder arranged between a screw and moving plate 16. The obtained primary compressed compact of the titanium fiber had the dimensions of 0.5 mm (thickness)×43 mm×13 mm.

The primary compressed compact of the titanium fiber was sandwiched by the magnesium powder from the top and the bottom and the secondary molding was conducted. When conducting the secondary molding, after depositing into a three-layered structure, this structure was set in a cold pressing/shearing device similar to the one described above and compressive stress P1 (compressive stress: 1250 MPa and compression load: 500 kN) was loaded. While remaining loaded with compressive stress P 1, moving plate 16 was moved in a lateral direction (shearing velocity: 5 mm/min and shearing distance: 5 mm) and then a secondary compressed compact having a three layered structure was produced. FIG. 14(C) is a schematic cross-sectional diagram illustrating an example of a compressed fiber structural material (the secondary compressed compact) in which the titanium fiber and the magnesium powder are compounded. The obtained secondary compressed compact had the dimensions of 0.56 mm (thickness)×43 mm×13 mm. It should be noted that the proportions between the titanium fiber and the magnesium powder configuring the secondary compressed compact were targeted at 95 volume % for the titanium fiber and 5 volume % for the magnesium powder.

(Dissolution Test and Strength after Dissolution Test)

The dissolution test of the obtained compressed fiber structural material was conducted, with reference to JIS H 0541, using saline (35° C.) with 0.9 volume % of sodium chloride at the times of 0, 30, 60, 180, 300 and 600 minutes. Approximately 30 minutes after the start of the test, bubbles were generated in the compressed fiber structural material. After the dissolution test, pores were observed on the surface of the compressed fiber structural material and thus, the dissolution of magnesium was observed.

The mechanical characteristics after the dissolution test were obtained by a tensile test. The tensile test complies with the former JIS Z 2201 and was conducted using a compact desk-top tester (available from Shimazu Corporation, model number: EZ-L-500N) with a testing rate of 0.5 mm/min at room temperature (25° C.). The test piece was made in accordance with the No. 7 test piece. A strain gauge (available from Kyowa Electronic Instruments Co., Ltd., model number: KGF-2-120-C1-11) was attached to a parallel portion of the test piece and the strain at the time of testing was measured and the measurement was used to derive a Young's modulus.

Table 7 shows the tensile strength and the Young's modulus over time resulting from the dissolution test. The strength of the composite compressed fiber structural material decreased as the dissolution time was prolonged. In particular, at the beginning, it demonstrated a value larger than that of the Young's modulus of in vivo bone; however, it then changed to a value which was the same as the Young's modulus of in vivo bone over time. Accordingly, due to the dissolution of the magnesium components, the mechanical characteristics of the composite compressed fiber structural material changed to mechanical characteristics comparable to those of in vivo bone.

TABLE 7

| | tensile strength (MPa)/Young's modulus (MPa) | | | | | |
|---|---|---|---|---|---|---|
| | 0 minutes | 30 minutes | 60 minutes | 180 minutes | 300 minutes | 600 minutes |
| compounded material | 80/20 | 75/20 | 68/18 | 70/19 | 68/18 | 68/15 |
| vivo bone | | | 85~105/10~17 | | | |

✕Time (minutes)

The feature of such compressed fiber structural material lies in the point that a titanium fiber and a magnesium powder are compounded through cold pressing/shearing. Thus, a desired strength can be provided while maintaining the functions of the titanium fiber and the magnesium powder. Moreover, the composite compressed fiber structural material can ensure the strength necessary for implantation at the time of initial implantation and then allows the strength thereof to approach the strength of in vivo bone through the dissolution of the magnesium components thereof after the implantation. In addition, since the titanium fiber is used as a base material, a desired strength can be maintained even after the dissolution of the magnesium components. Further, since magnesium is biocompatible, it has no adverse effect on the human body.

DESCRIPTIONS OF REFERENCE NUMERALS

1 Compressed fiber structural material
10 Fixed plate
12 Penetrated mold
13 Penetration hole
14 Biocompatible fiber
16 Moving plate
20 cold pressing/shearing device
21 Load cell
23 Strain gauge
25 Displacement gauge
31-34 Plate
P1 Compressive stress
P2 Shearing stress
d shearing stroke length
$t_A$ Fill height of the biocompatible fiber
$L_A$ Fill length of the biocompatible fiber
$t_B$ Thickness of the compressed fiber structural material
$L_B$ Length of the compressed fiber structural material

The invention claimed is:

1. A method for producing a compressed fiber structural material, comprising:
    a step of preparing a biocompatible fiber having an average diameter of 5 μm-50 μm and an aspect ratio of 20-500; and
    a step of molding a compressed fiber structural material by cold pressing/shearing the biocompatible fiber, the compressed fiber structural material having an average pore diameter that is in the range of 60 μm-100 μm inclusive and a void fraction that is in the range of 25%-50% inclusive, both obtained by measurement in accordance with the mercury penetration method, wherein
    a titanium fiber is used as the biocompatible fiber, and
    the step of molding a compressed fiber structural material includes:
        a step of obtaining the primary compressed compact by cold pressing/shearing the biocompatible fiber; and
        a step of secondary-molding the primary compressed compact that is sandwiched by the magnesium powder from the top and the bottom or that has the magnesium powder deposited on either one of the top and the bottom.

2. The method for producing a compressed fiber structural material according to claim 1, wherein
    the cold pressing/shearing is performed by controlling a compressive pressure in the range of 200 MPa-2000 MPa, a shearing stroke length in the range of 0.2 mm-5 mm and a shearing velocity in the range of 0.5 mm/min-5 mm/min.

3. The method for producing a compressed fiber structural material according to claim 1, wherein
    a bulk density of the compressed fiber structural material is controlled so as to be in the range of 3 g/cm³-5 g/cm³.

4. A compressed fiber structural material, comprising:
    a biocompatible fiber having an average diameter of 5 μm-50 μm and an aspect ratio of 20-500, the biocompatible fiber being compressed and solidified without sintering, the biocompatible fiber being a titanium fiber as a compressed compact;
    magnesium powders deposited on at least one of the top surface and the bottom surface of the compressed compact, the magnesium powders being compressed and solidified without sintering; and
    an average pore diameter in the range of 60 μm-100 μm inclusive and a void fraction in the range of 25%-50% inclusive, both of the average pore diameter and the void fraction being obtained by measurement in accordance with the mercury penetration method.

5. The compressed fiber structural material according to claim 4, wherein
    a bulk density of the compressed fiber structural material is controlled so as to be in the range of 3 g/cm³-5 g/cm³.

* * * * *